United States Patent
Etzkorn et al.

(10) Patent No.: US 9,770,207 B2
(45) Date of Patent: Sep. 26, 2017

(54) SENSOR ELECTRODES IN A BIO-COMPATIBLE DEVICE

(71) Applicant: Verily Life Sciences LLC, Mountain View, CA (US)

(72) Inventors: James Etzkorn, Mountain View, CA (US); Harvey Ho, San Francisco, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 804 days.

(21) Appl. No.: 14/139,855

(22) Filed: Dec. 23, 2013

(65) Prior Publication Data

US 2015/0173680 A1   Jun. 25, 2015

(51) Int. Cl.
*A61B 5/1486* (2006.01)
*A61B 5/00* (2006.01)
*A61B 5/145* (2006.01)

(52) U.S. Cl.
CPC .......... *A61B 5/6821* (2013.01); *A61B 5/0002* (2013.01); *A61B 5/1486* (2013.01); *A61B 5/14532* (2013.01); *Y10T 29/49155* (2015.01)

(58) Field of Classification Search
CPC . A61B 5/6821; A61B 5/0002; A61B 5/14532; A61B 5/1486; Y10T 29/49155
See application file for complete search history.

(56) References Cited

U.S. PATENT DOCUMENTS

| | | | | |
|---|---|---|---|---|
| 5,782,761 A | * | 7/1998 | Gusakov | A61B 5/04087 600/391 |
| 6,707,610 B1 | * | 3/2004 | Woodard | B32B 17/10018 359/582 |
| 6,828,059 B2 | * | 12/2004 | Miller | H01M 10/0431 429/127 |
| 7,941,201 B2 | | 5/2011 | Chiou et al. | |
| 8,460,922 B2 | | 6/2013 | Miller et al. | |
| 2002/0192558 A1 | * | 12/2002 | Miller | H01M 10/0431 429/233 |

(Continued)

FOREIGN PATENT DOCUMENTS

| WO | 2004027465 A1 | | 4/2004 | |
|---|---|---|---|---|
| WO | WO 201309191 | * | 6/2013 | ............ A41D 31/00 |

OTHER PUBLICATIONS

Yao et al. "A contact lens with embedded sensor for monitoring tear glucose level." Biosens Bioelectron. Mar. 15, 2011;26(7):3290-6. doi: 10.1016/j.bios.2010.12.042. Epub Dec. 31, 2010.*

(Continued)

*Primary Examiner* — Meredith Weare
(74) *Attorney, Agent, or Firm* — McDonnell, Boehnen Hulbert & Berghoff LLP

(57) ABSTRACT

A method may involve providing a conductive pattern on a bio-compatible layer. The conductive pattern may include a first conductive layer that comprises a first metal and a second conductive layer that comprises a second metal. The second conductive layer may be over the first conductive layer, and the first metal may be more malleable than the second metal. The method may also include mounting an electrical component to the conductive pattern to provide an electrochemical sensor. The electrochemical sensor may be configured for use in a body-mountable device.

14 Claims, 13 Drawing Sheets

(56) References Cited

U.S. PATENT DOCUMENTS

| | | | |
|---|---|---|---|
| 2005/0051427 A1* | 3/2005 | Brauker | A61B 5/076 204/412 |
| 2007/0142878 A1* | 6/2007 | Krulevitch | A61N 1/0543 607/54 |
| 2008/0296155 A1* | 12/2008 | Shults | A61B 5/0002 204/403.11 |
| 2009/0091698 A1 | 4/2009 | Cho | |
| 2009/0198117 A1 | 8/2009 | Cooper et al. | |
| 2010/0285514 A1 | 11/2010 | Claussen et al. | |
| 2010/0292551 A1 | 11/2010 | Jina | |
| 2011/0045577 A1 | 2/2011 | Bruzewicz et al. | |
| 2011/0077490 A1 | 3/2011 | Simpson et al. | |
| 2011/0201312 A1 | 8/2011 | Peterson et al. | |
| 2012/0245444 A1 | 9/2012 | Otis et al. | |
| 2014/0374262 A1* | 12/2014 | Heldal | A41D 31/0016 204/639 |

OTHER PUBLICATIONS

Cheng et al. "Metabolic monitoring of the electrically stimulated single heart cell within a microfluidic platform." Lab Chip. Nov. 2006;6(11):1424-31. Epub Sep. 14, 2006.*

International Search Report and Written Opinion for International Application No. PCT/US2014/071985 dated Mar. 30, 2015.

* cited by examiner

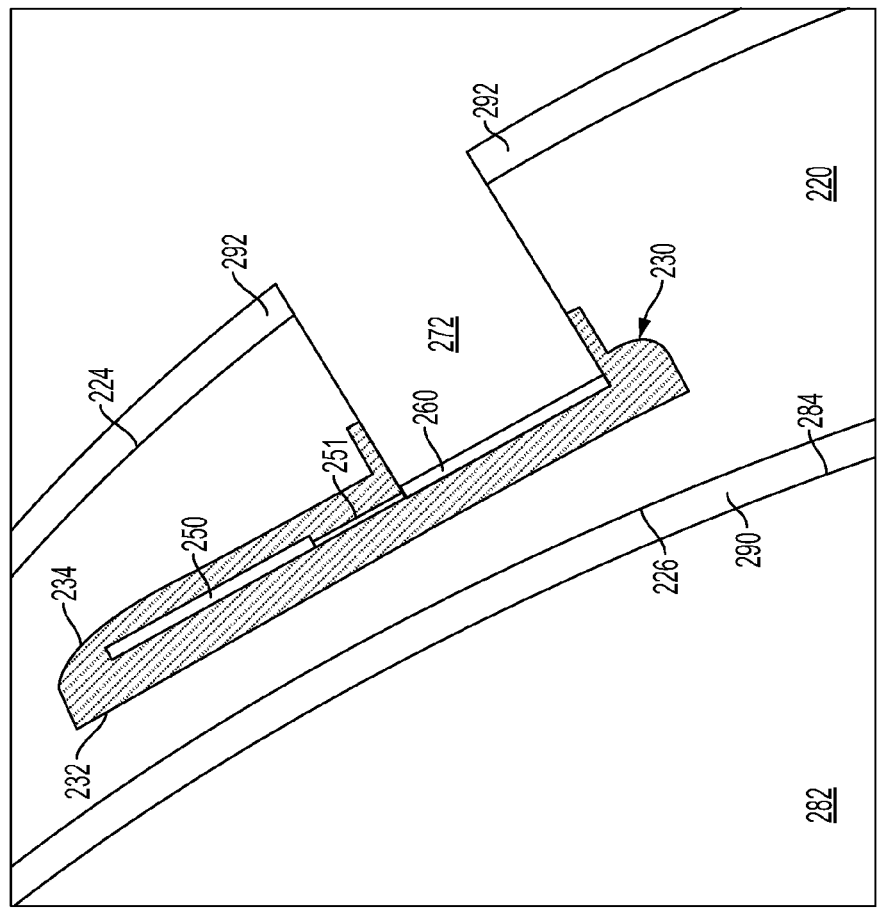
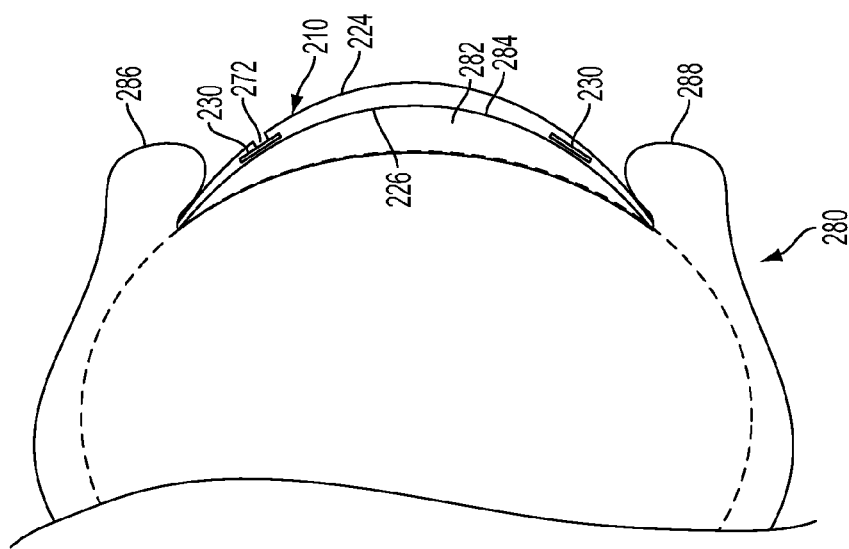
FIG. 2d
FIG. 2c

SENSOR ELECTRODES IN A BIO-COMPATIBLE DEVICE

BACKGROUND

Unless otherwise indicated herein, the materials described in this section are not prior art to the claims in this application and are not admitted to be prior art by inclusion in this section.

A body-mountable device may be configured to monitor health-related information based on at least one analyte from a user. For example, a bio-compatible device may be embedded in a polymer to provide the body-mountable device. The bio-compatible device includes a sensor configured to detect the at least one analyte (e.g., glucose) in a fluid of a user wearing the body-mountable device. The body-mountable device may also be configured to monitor various other types of health-related information.

SUMMARY

In one aspect, a method involves providing a conductive pattern on a bio-compatible layer to provide at least one sensor electrode. The at least one sensor electrode may include a first conductive layer that comprises a first metal and a second conductive layer that comprises a second metal. The second conductive layer may be over the first conductive layer, and the first metal may be more malleable than the second metal. Additionally, the method involves mounting an electronic component to the conductive pattern to provide at least an electrochemical sensor. The electrochemical sensor may be configured for use in a body-mountable device.

In another aspect, a sensor includes a conductive pattern on a bio-compatible layer and an electronic component. The conductive pattern may comprise at least one sensor electrode. The at least one sensor electrode may include a first conductive layer that comprises a first metal and a second conductive layer that comprises a second metal. The second conductive layer may be over the first conductive layer, and the first metal maybe more malleable than the second metal. Further, the sensor may be configured for use as an electrochemical sensor in a body-mountable device.

In yet another aspect, a system is disclosed. The system comprises means for providing a conductive pattern on a bio-compatible layer to provide at least one sensor electrode. To provide the at least one sensor electrode, the system may further comprise means for providing a first conductive layer and a second conductive layer, with the second conductive layer being over the first conductive layer. The first conductive layer may comprise a first metal, and the second conductive layer may comprise a second metal. The first metal may be more malleable than the second metal. The system may also include means for mounting an electronic component to the conductive pattern to provide at least an electrochemical sensor configured for use in a body-mountable device.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2c is a side cross-section view of the eye-mountable device of FIG. 2a while mounted to a corneal surface of the eye, according to an example embodiment.

FIG. 2d is a side cross-section view showing the tear film layers surrounding the surfaces of the eye-mountable device mounted as shown in FIG. 2c, according to an example embodiment.

DETAILED DESCRIPTION

The following detailed description describes various features and functions of the disclosed methods and systems with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

I. Introduction

A bio-compatible device may include a first bio-compatible layer, a conductive pattern on the first bio-compatible layer, an electronic component mounted to the conductive pattern, and a second bio-compatible layer over the first bio-compatible layer, the electronic component, and the conductive pattern.

A portion of the conductive pattern may provide at least one sensor electrode. The at least one sensor electrode may be connected to an electrical component to form at least an electrochemical sensor. The at least one sensor electrode may include a first conductive layer that comprises a first metal and a second conductive layer that comprises a second metal. The second conductive layer, which may be over the first conductive layer, may provide a surface for a reduction reaction or an oxidation reaction. Based on the application, however, the second metal may be susceptible to cracking during fabrication of the bio-compatible device, which may impact the functionality of the electrochemical sensor. For instance, cracks in the second conductive layer may not provide a continuous electrical pathway from the at least one sensor electrode to the electronic component.

Beneficially, embodiments described herein may improve the performance of the electrochemical sensor by providing a substantially continuous electrical pathway between the electronic component and the at least one sensor electrode. The first metal may be more malleable than the second metal. In this manner, the first conductive layer may be less susceptible to cracking during the fabrication of the bio-compatible device, thereby providing a substantially continuous pathway between the electronic component and the at least one sensor electrodes.

II. Example Systems and Devices

An example body-mountable device that comprises an eye-mountable device that is configured to detect at least one analyte in a tear film of a user wearing the eye-mountable device will now be described in greater detail.

Figure 1:
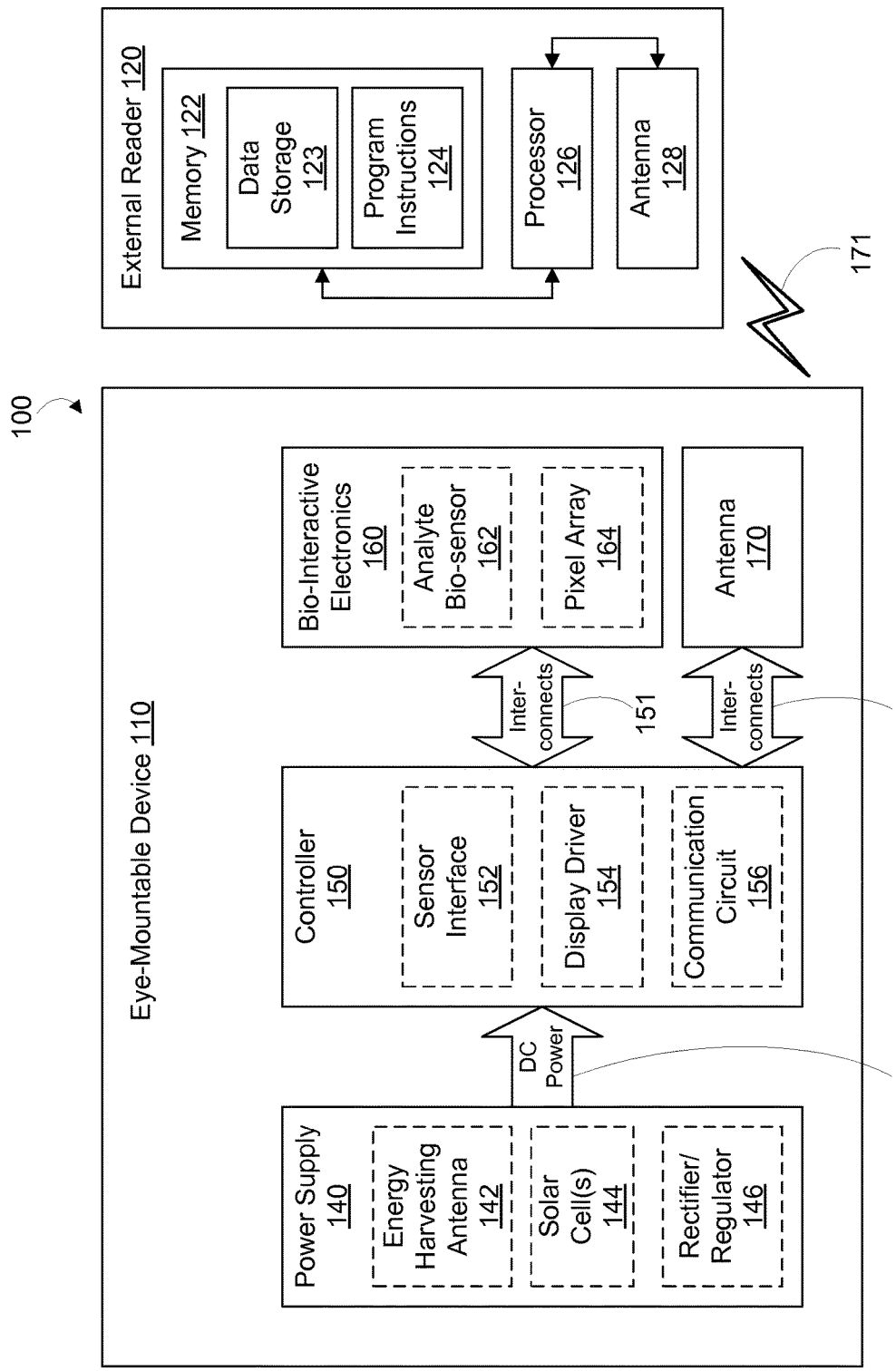
FIG. 1 is a block diagram of a system with an eye-mountable device in wireless communication with an external reader, according to an example embodiment.

FIG. 1 is a block diagram of a system 100 that includes an eye-mountable device 110 in wireless communication with an external reader 120. The eye-mountable device 110 may be a polymeric material that may be appropriately shaped for mounting to a corneal surface and in which a structure is at least partially embedded. The structure may include a power supply 140, a controller 150, bio-interactive electronics 160, and an antenna 170.

In some embodiments, the structure may be a bio-compatible device in which some or all of the components formed or mounted thereon are encapsulated by a biocompatible material.

In some example embodiments, the structure may be positioned away from the center of the eye-mountable device 110 and thereby avoid interference with light transmission to the central, light-sensitive region of the eye. For example, where the eye-mountable device 110 is shaped as a curved disk, the structure may be embedded around the periphery (e.g., near the outer circumference) of the disk. In other example embodiments, the structure may be positioned in or near the central region of the eye-mountable device 110. For example, portions of the structure may be substantially transparent to incoming visible light to mitigate interference with light transmission to the eye. Moreover, in some embodiments, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the energy harvesting antenna 142 and/or solar cell(s) 144. For example, one or more energy storage devices (e.g., a capacitor or an inductor) may be connected in parallel across the outputs of the rectifier/regulator 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOX") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

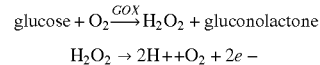

$$\text{glucose} + O_2 \xrightarrow{GOX} H_2O_2 + \text{gluconolactone}$$
$$H_2O_2 \rightarrow 2H+ + O_2 + 2e-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 may also include a display driver module 154 for operating a pixel array 164. The pixel array 164 is an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 may also include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 may also include a communication circuit 156 for sending and/or receiving information via the antenna 170. The communication circuit 156 may include one or more oscillators, mixers, frequency injectors, or the like to modulate and/or demodulate information on a carrier frequency to be transmitted and/or received by the antenna 170. In some example embodiments, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 via interconnects 151. Similarly, the controller 150 is connected to the antenna 170 via interconnects 157. The interconnects 151, 157 may comprise a patterned conductive material (e.g., gold, platinum, palladium, titanium, copper, aluminum, silver, metals, any combinations of these, etc.).

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component.

Additionally or alternatively, the energy harvesting antenna 142 and the antenna 170 can be implemented in the same, dual-purpose antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g., RAM) or non-volatile (e.g., ROM) storage system readable by the processor 126. The memory 122 includes a data storage 123 to store indications of data, such as sensor readings (e.g., from the analyte bio-sensor 162), program settings (e.g., to adjust behavior of the eye-mountable device 110 and/or external reader 120), etc. The memory 122 also includes program instructions 124 for execution by the processor 126. For example, the program instructions 124 may cause the external reader 120 to provide a user interface that allows for retrieving information communicated from the eye-mountable device 110 (e.g., sensor outputs from the analyte bio-sensor 162). The external reader 120 may also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 may also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using little or low power. For example, the external reader 120 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 120 (e.g., via the communication circuit 156).

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 2A:
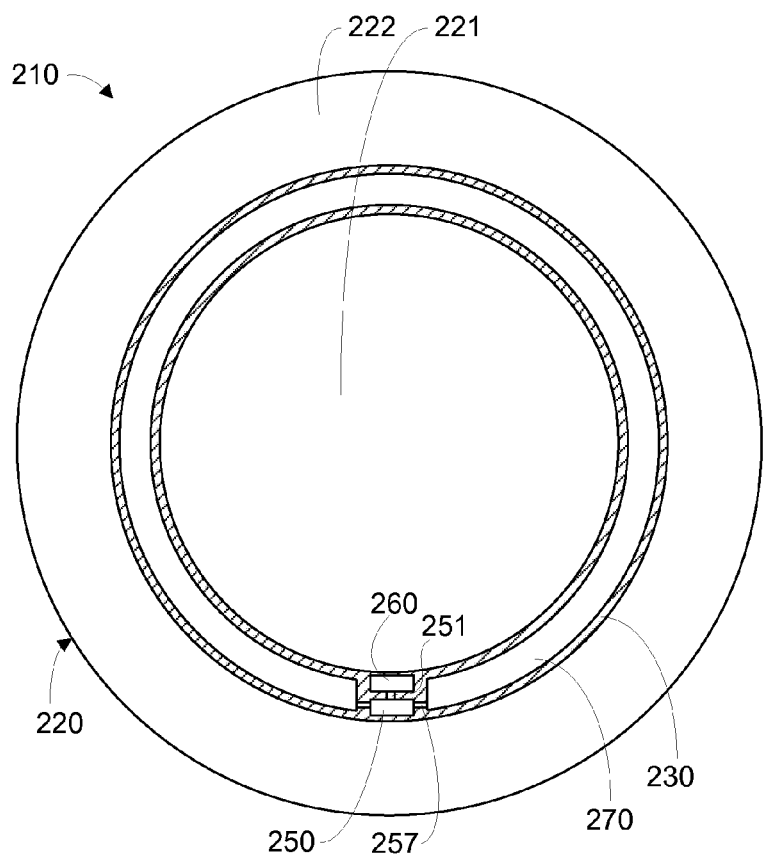
FIG. 2a is a top view of an eye-mountable device, according to an example embodiment.
Figure 2B:
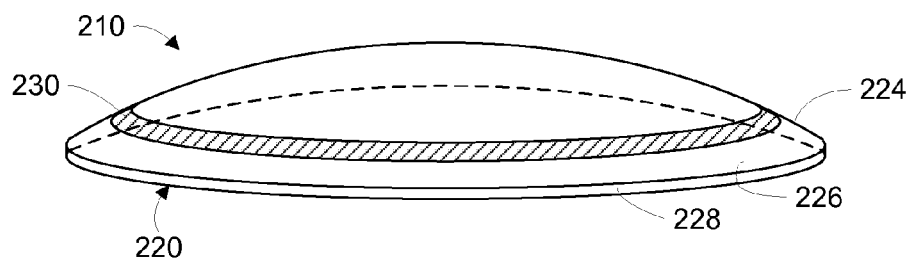
FIG. 2b is a side view of an eye-mountable device, according to an example embodiment.

FIG. 2a is a top view of an eye-mountable device 210. FIG. 2b is side view of the eye-mountable device 210. It is noted that relative dimensions in FIGS. 2a and 2b are not necessarily to scale, but have been rendered for purposes of explanation only in describing the arrangement of the eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, or any combinations of these. Other polymeric materials may also be envisioned. The polymeric material 220 may include materials configured to moisturize the corneal surface, such as hydrogels and the like. In some embodiments, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). While mounted with the concave surface against the eye, a convex surface 224 of eye-mountable device 210 is formed so as not to interfere with eye-lid motion while the eye-mountable device 210 is mounted to the eye. A circular outer side edge 228 connects the concave surface 224 and the convex surface 226. The convex surface 224 can therefore be considered an outer, top surface of the eye-mountable device 210 whereas the concave surface 226 can be considered an inner, bottom surface. The "top" view shown in FIG. 2a is facing the convex surface 224.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 may be selected according to the size and/or shape of the corneal surface and/or the scleral surface of the wearer's eye. In some embodiments, the eye-mountable device 210 is shaped to provide a predetermined, vision-correcting optical power, such as provided by a prescription contact lens.

A structure 230 is embedded in the eye-mountable device 210. The structure 230 can be embedded to be situated near or along an outer periphery 222, away from a central region 221. Such a position ensures that the structure 230 will not interfere with a wearer's vision when the eye-mountable device 210 is mounted on a wearer's eye, because it is positioned away from the central region 221 where incident light is transmitted to the light-sensing portions of the eye. Moreover, portions of the structure 230 can be formed of a transparent material to further mitigate effects on visual perception.

The structure 230 may be shaped as a flat, circular ring (e.g., a disk with a centered hole). The flat surface of the structure 230 (e.g., along the radial width) allows for mounting electronics such as chips (e.g., via flip-chip mounting) and for patterning conductive materials to form electrodes, antenna(e), and/or interconnections. The structure 230 and the polymeric material 220 may be approximately cylindrically symmetric about a common central axis. The structure 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit this disclosure.

A loop antenna 270, controller 250, and bio-interactive electronics 260 are included in the structure 230. The controller 250 may be a chip including logic elements configured to operate the bio-interactive electronics 260 and the loop antenna 270. The controller 250 is electrically connected to the loop antenna 270 by interconnects 257 also situated on the structure 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that can be used for patterning such materials, such as deposition or photolithography, for example. The conductive materials patterned on the structure 230 may be, for example, gold, platinum, palladium, titanium, carbon, aluminum, copper, silver, silver-chloride, conductors formed from noble materials, metals, or any combinations of these materials. Other materials may also be envisioned.

The structure 230 may be a bio-compatible device in which some or all of the components are encapsulated by a bio-compatible material. In one example, the controller 250, interconnects 251, 257, bio-interactive electronics 260, and the loop antenna 270 are fully encapsulated by bio-compatible material, except for the sensor electrodes in the bio-interactive electronics 260.

As shown in FIG. 2a, the bio-interactive electronics module 260 is on a side of the structure 230 facing the convex surface 224. Where the bio-interactive electronics module 260 includes an analyte bio-sensor, for example, mounting such a bio-sensor on the structure 230 to be close to the convex surface 224 allows the bio-sensor to sense analyte that has diffused through convex surface 224 or has reached the bio-sensor through a channel in the convex surface 224 (FIGS. 2c and 2d show a channel 272).

The loop antenna 270 is a layer of conductive material patterned along the flat surface of the structure 230 to form a flat conductive ring. In some example embodiments, the loop antenna 270 does not form a complete loop. For example, the loop antenna 270 may include a cutout to allow room for the controller 250 and bio-interactive electronics 260, as illustrated in FIG. 2a. However, in another example embodiment, the loop antenna 270 can be arranged as a continuous strip of conductive material that wraps entirely around the structure 230 one or more times. Interconnects between the ends of such a wound antenna (e.g., the antenna leads) can connect to the controller 250 in the structure 230. In some embodiments, the loop antenna can include a plurality of conductive loops spaced apart from each other, such as three conductive loops, five conductive loops, nine conductive loops, etc. With such an arrangement, the polymeric material 220 may extend between adjacent conductive loops in the plurality of conductive loops.

FIG. 2c is a side cross-section view of the eye-mountable electronic device 210 mounted to a corneal surface 284 of an eye 280. FIG. 2d is an enlarged partial view of the cross-section of the eye-mountable device shown in FIG. 2c. It is noted that relative dimensions in FIGS. 2c and 2d are not necessarily to scale, but have been rendered for purposes of explanation only in describing the arrangement of the eye-mountable device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the concave and convex surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2c and 2d, the structure 230 can be inclined so as to be approximately parallel to the adjacent portion of the convex surface 224. As described above, the structure 230 is a flattened ring with an inward-facing surface 232 (closer to the concave surface 226 of the polymeric material 220) and an outward-facing surface 234 (closer to the convex surface 224). The structure 230 can include electronic components and/or patterned conductive materials adjacent to either or both surfaces 232, 234.

As shown in FIG. 2d, the bio-interactive electronics 260, the controller 250, and the conductive interconnect 251 are located between the outward-facing surface 234 and the inward-facing surface 632 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the structure 230 such that the bio-interactive electronics 260 are facing the concave surface 226.

While the body-mountable device has been described as comprising the eye-mountable device 110 and/or the eye-mountable device 210, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 210. For instance, the tooth-mountable device could include a polymeric material that is the same as or similar to any of the polymeric materials described herein and a structure that is the same as or similar to any of the structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 210. For instance, the skin-mountable device could include a polymeric material that is the same as or similar to any of the polymeric materials described herein and a structure that is the same as or similar to any of the structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Methods

Figure 3A:
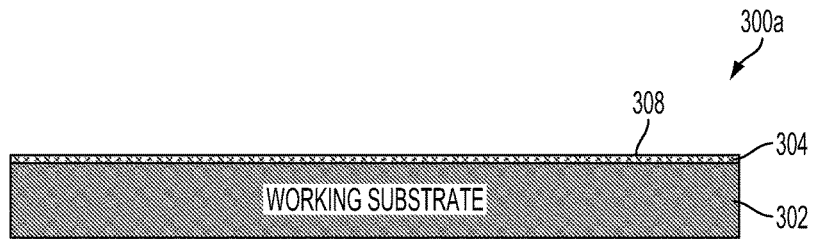
FIGS. 3a-r show stages of fabricating a bio-compatible device, according to an example embodiment.
Figure 3B:
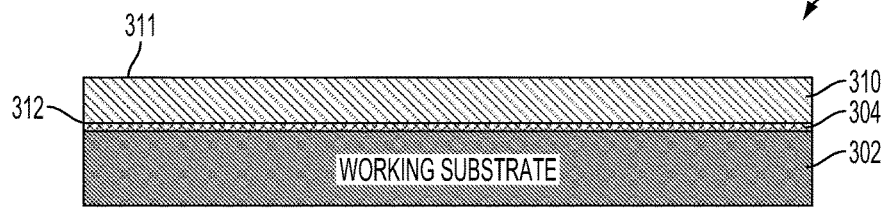
Figure 3C:
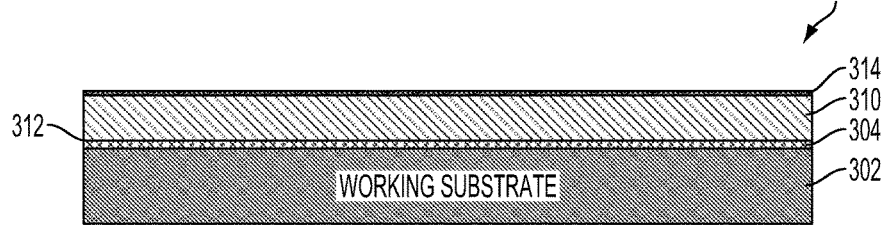
Figure 3D:
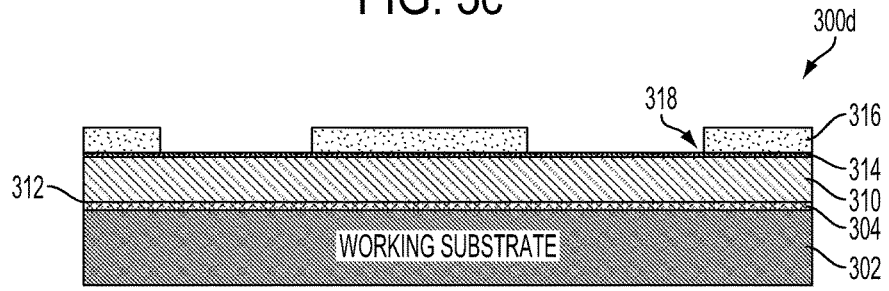
Figure 3E:
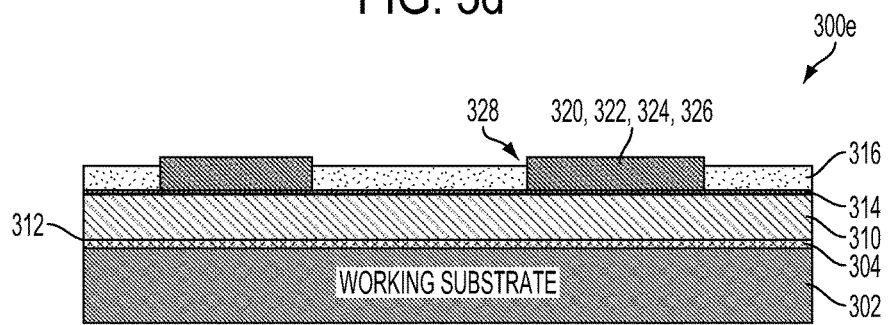
Figure 3F:
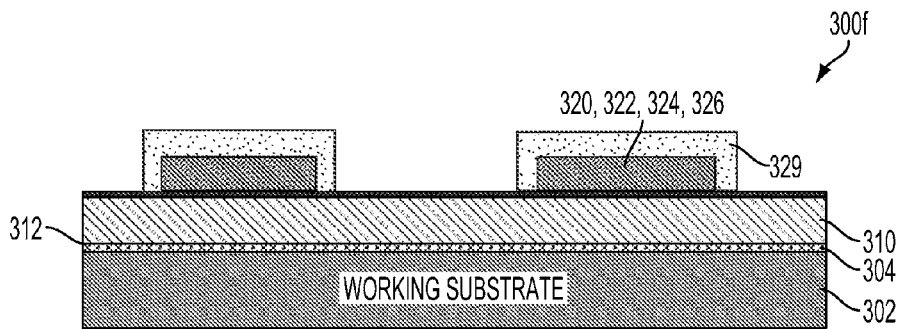
Figure 3G:
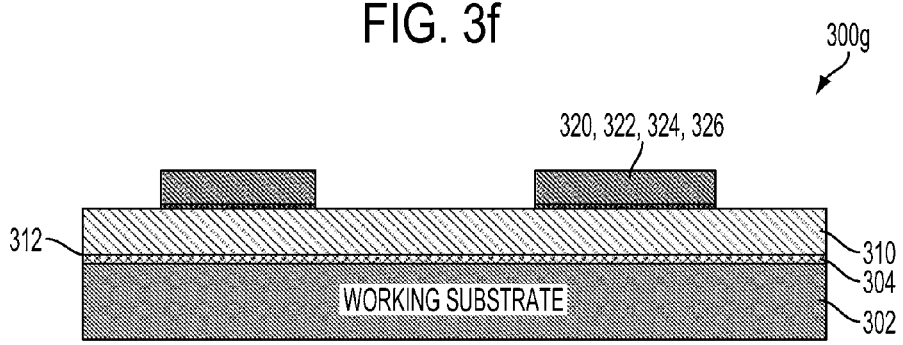
Figure 3H:
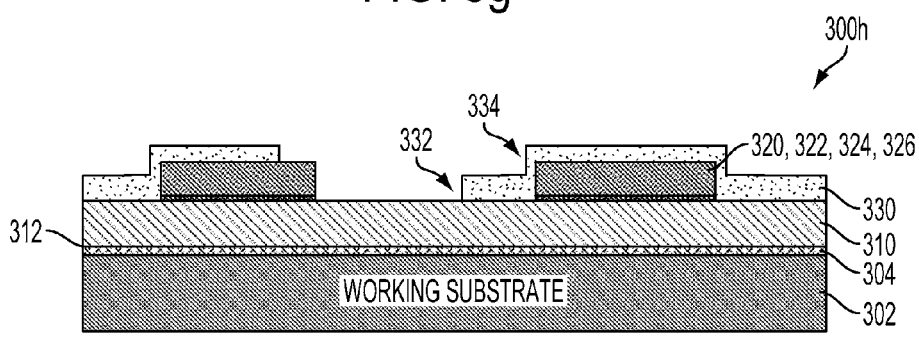
Figure 3I:
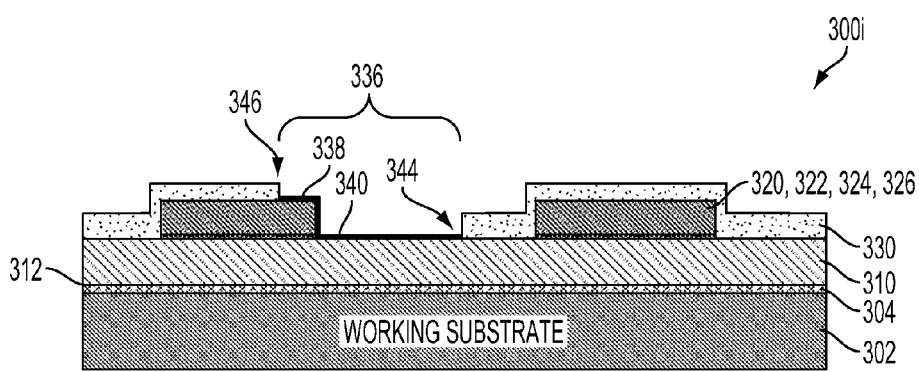
Figure 3J:
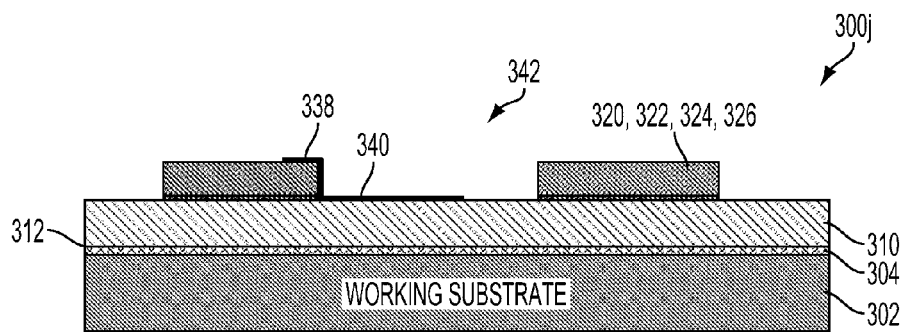
Figure 3K:
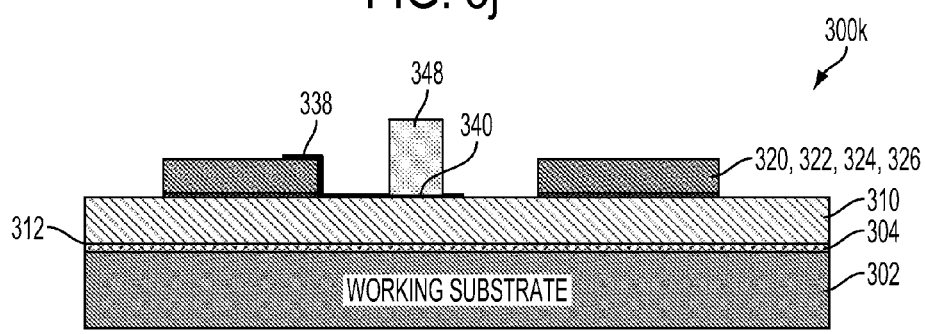
Figure 3L:
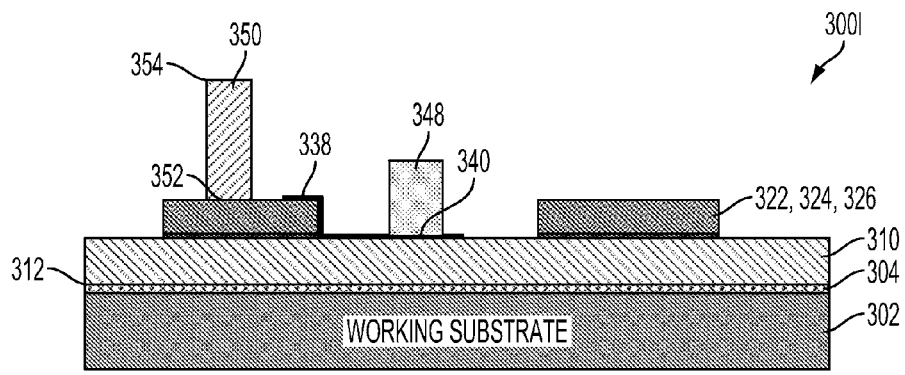
Figure 3M:
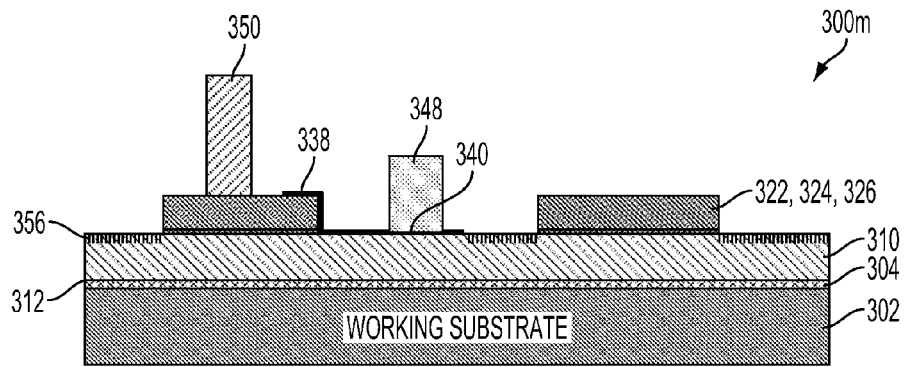
Figure 3N:
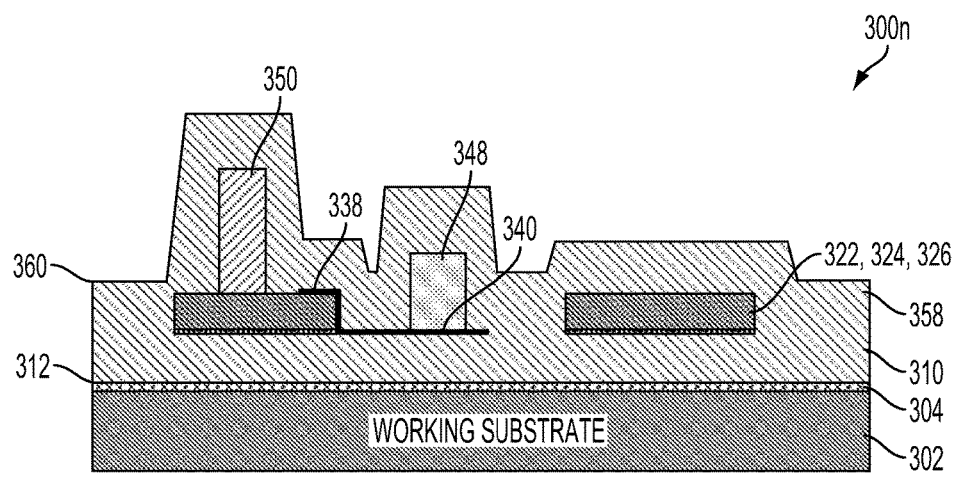
Figure 3O:
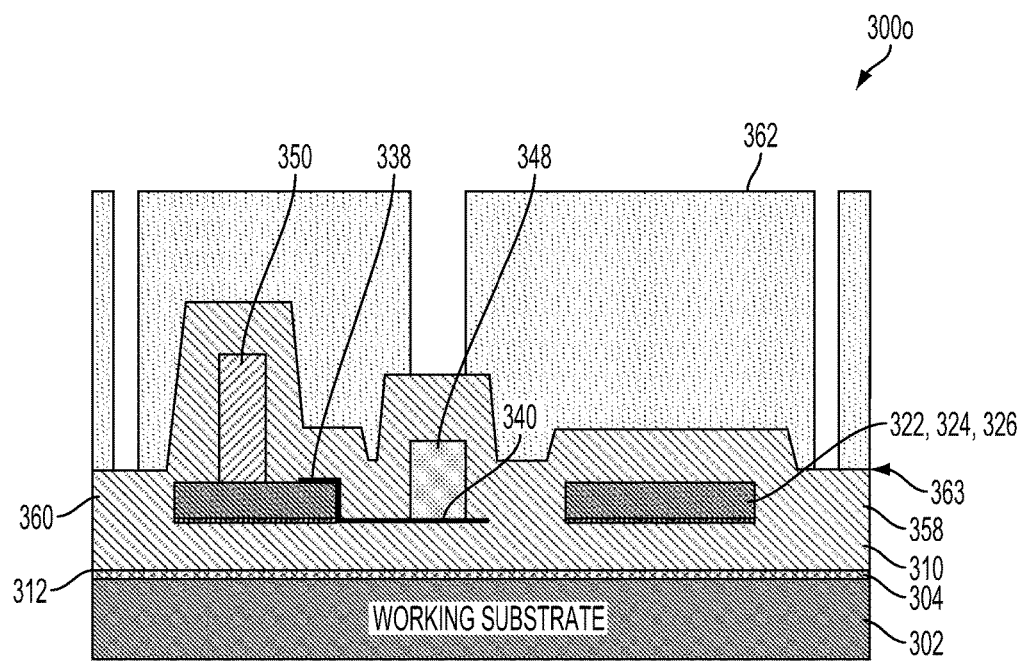
Figure 3P:
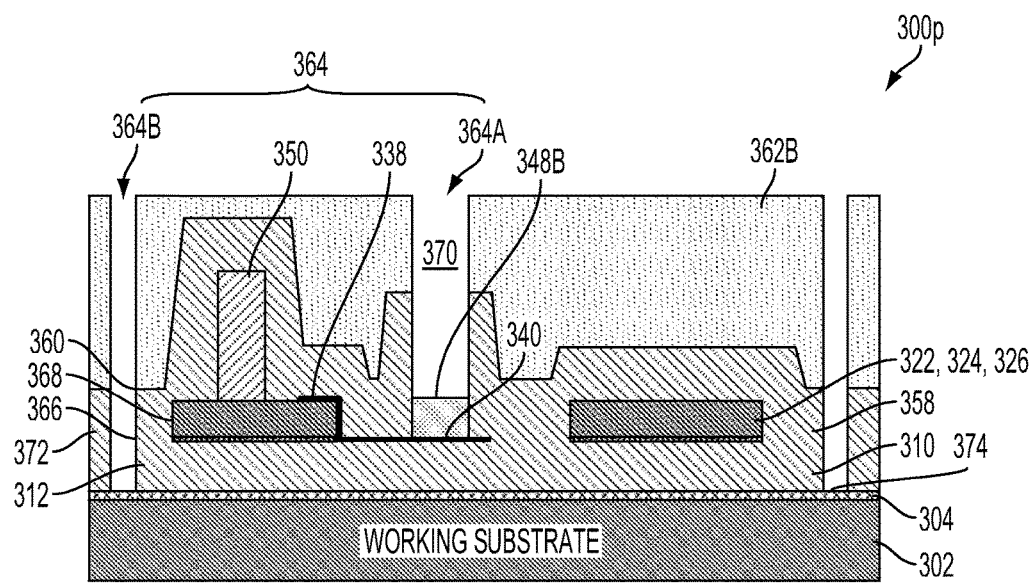
Figure 3Q:
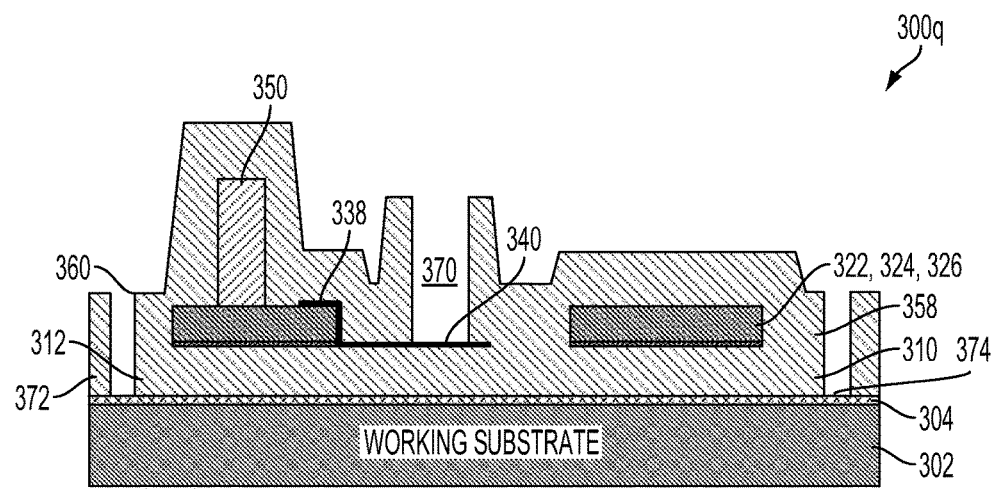
Figure 3R:
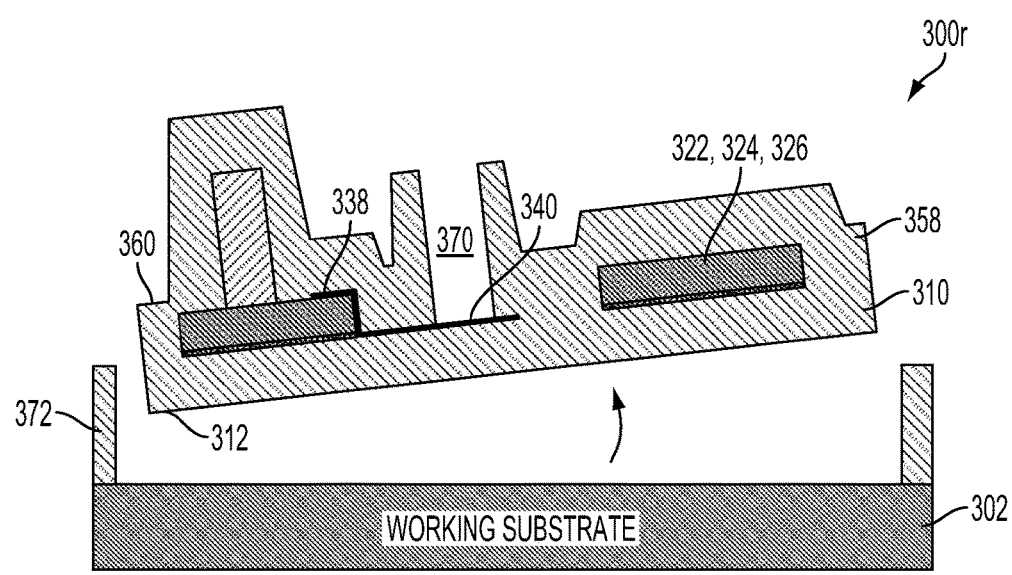

FIGS. 3a-r illustrate stages in a process for fabricating a bio-compatible device, such as a bio-compatible device 300r shown in FIG. 3r. The illustrations shown in FIGS. 3a-r are generally shown in cross-sectional views to illustrate sequentially formed layers developed to create the bio-compatible device. The layers can be developed by microfabrication and/or manufacturing techniques such as, for example, electroplating, photolithography, deposition, and/or evaporation fabrication processes and the like. The various materials may be formed according to patterns using photoresists and/or masks to pattern materials in particular arrangements, such as to form wires, electrodes, electrical contacts, etc. Additionally, electroplating techniques may also be employed to coat an arrangement of electrodes with a metallic plating. For example, an arrangement of conductive material formed by a deposition and/or photolithography process can be plated with a metallic material to create a conductive structure with a desired thickness. However, the dimensions, including relative thicknesses and widths, of the various layers illustrated and described in connection with FIGS. 3a-r to create a bio-compatible device are not illustrated to scale. Instead, the drawings in FIGS. 3a-r schematically illustrate the ordering of the various layers for purposes of explanation only.

FIG. 3a illustrates a working substrate 302 with a sacrificial layer 304 formed on the working substrate 302 to provide a partially-fabricated device 300a. The sacrificial layer 304 may have a surface 308.

The working substrate 302 may be any flat surface on which the layers of the encapsulated electronics structure can be assembled. For example, the working substrate 302 may be a wafer (e.g., a silicon wafer) similar to those used in the fabrication of semiconductor devices and/or microelectronics.

The sacrificial layer 304 could take various different forms in various different embodiments. Example sacrificial layers that may be formed on the working substrate 302 are described with reference to FIGS. 4-9.

In some embodiments, the sacrificial layer 304 may adhere to the working substrate 302. Moreover, in some embodiments, a bio-compatible layer formed on the sacrificial layer 304 may adhere to the sacrificial layer 304.

Moreover, the working substrate 302 may be cleaned before forming the sacrificial layer 304. The working substrate 302 may be cleaned in a variety of ways. For example, the working substrate 302 may be cleaned by soaking in a first fluid, rinsing with a second fluid, and drying with a gas. In some embodiments, the first fluid may include a solvent, such as acetone. Moreover, in some embodiments, the second fluid may include isopropyl alcohol (IPA). Further, in some embodiments, the gas may include nitrogen. All of the rinsing described herein may be performed in a variety ways, such as soaking in a bath in a tank, an automated spray, manually via a squirt bottle, etc.

Further, the working substrate 302 may be baked before forming the sacrificial layer 304. The working substrate 302 may be baked in a variety of ways. For example, the working substrate 302 may be baked at a temperature for a time period. In some embodiments, the temperature may be 90° Celsius (C). Moreover, in some embodiments, the time period may be 2 minutes.

Further still, the working substrate 302 may be plasma cleaned before forming the sacrificial layer 304. The working substrate 302 may be plasma cleaned in a variety of ways. For example, the working substrate 302 may be plasma cleaned at a power for a time period. In some embodiments, the power may be high. Moreover, in some embodiments, the time period may be 5 minutes.

As shown in FIG. 3b, a first bio-compatible layer 310 is formed on the sacrificial layer 304 to provide a partially-fabricated device 300b. The first bio-compatible layer 310 may be formed on the sacrificial layer 304, such that the first bio-compatible layer 310 adheres to the sacrificial layer 304. The first bio-compatible layer 310 defines a first side 312 of a bio-compatible device. That is, the first bio-compatible layer 310 defines an outer edge of the bio-compatible device.

The first bio-compatible layer 310 may include a variety of materials. For example, the first bio-compatible layer 310 may include a polymeric material such as SCS parylene-C (e.g., dichlorodi-p-xylylene), a polyethylene terephthalate (PET), a polydimethysiloxane (PDMS), other silicone elastomers, and/or another bio-compatible polymeric material. The term "bio-compatibility," as used in this disclosure, refers generally to the ability of a material or device to co-exist with a biological host. Bio-compatible materials are generally those that do not bring about a host response (such as an immune response) that results in deleterious effects to either the biological host or the material. In addition to being bio-compatible, the first bio-compatible layer 310 may be an electrically insulating material to isolate encapsulated electronics from the surrounding environment (e.g., from current-carrying particles and/or fluids).

Moreover, the first bio-compatible layer 310 may have a variety of thicknesses. For example, the first bio-compatible layer 310 may have a thickness between 5 to 50 micrometers, such as 15 micrometers. Other thicknesses of the first bio-compatible layer 310 are possible as well.

In an example, the first bio-compatible layer 310 may be formed by a microfabrication process such as chemical vapor deposition, and provides a surface on which various components can be formed. The first bio-compatible layer 310 may be deposited onto the sacrificial layer 304 with a substantially uniform thickness such that a surface of the first bio-compatible layer 310 opposite the working substrate 302 forms a flat surface. In addition, the first bio-compatible layer 310 may have sufficient structural rigidity to be used as a substrate for assembling various components. In some embodiments, the first bio-compatible layer 310 may be a conformal coat.

In an example, equipment that forms the first bio-compatible layer 310 may be preheated for 1 hour before forming the first bio-compatible layer 310. Moreover, in an example, 35 grams of a polymeric material may be used to form the first bio-compatible layer 310.

Moreover, an adhesion promoter may be applied to a surface of the sacrificial layer 304 before the first bio-compatible layer 310 is formed. With such an arrangement, adhesion of the first bio-compatible layer 310 to the sacrificial layer 304 may be improved. For example, an adhesion promoter may be applied to the surface 308 of the sacrificial layer 304.

In some embodiments, the adhesion promoter may comprise 3-methacryloyloxypropyltrimethoxysilane. And in such embodiments, the adhesion promoter may be A174 sold by Specialty Coating Systems and/or Sigma Aldrich. Moreover, in some embodiments, the adhesion promoter may comprise hexamethyldisilazane (HDMS). Other adhesion promoters are possible as well.

The adhesion promoter may be applied in a variety of ways. For example, the adhesion promoter may be applied by spin coating at a rate, baking at a temperature for a first time period, rinsing with a fluid, and baking at the temperature for a second time period. In some embodiments, the rate may be 3000 rotations per minute (rpm). And in such embodiments, applying the adhesion promoter by spin coating may involve accelerating and/or decelerating the partially-fabricated device 300a at a rate between 100 to 3000 rpm per second, such as 1000 to 1500 rpm per second. Moreover, in some embodiments, the temperature may be 90° C. Further, in some embodiments, the first time period may be 2 minutes. Further still, in some embodiments, the fluid may include IPA. And, in some embodiments, the second time period may be 1 minute.

In another example, the adhesion promoter may be applied by soaking the partially-fabricated device 300a in a mixture including the adhesion promoter for a first time period, air drying on a towel for a second time period, rinsing with one or more fluids, and drying with a gas. In some embodiments, the mixture may comprise 100 parts deionized water (DI water), 100 parts IPA, and 1 part the adhesion promoter. Moreover, in some embodiments, the mixture may settle for 2 hours before soaking the partially-fabricated device 300a in the mixture. Further, in some embodiments, the first time period may be 30 minutes. Moreover, in some embodiments, the second time period may be 30 minutes. Further, in some embodiments, the one or more fluids may include IPA and DI water. And, in some embodiments, the gas may include nitrogen. In such an example, soaking the partially-fabricated device 300a in a mixture including the adhesion promoter for the first time period, air drying on a towel for the second time period, rinsing with one or more fluids, and/or drying with the gas may occur at room temperature. Moreover, in such an example, applying the adhesion promoter may further involve baking the partially-fabricated device 300a at a temperature for a time period. In some embodiments, the temperature may be 90° C. Moreover, in some embodiments, the time period may be 2 minutes.

Moreover, the partially-fabricated device 300a may be cleaned before applying the adhesion promoter to a surface of the sacrificial layer 304. The partially-fabricated device 300a may be cleaned in a variety of ways. For example, the partially-fabricated device 300a may be cleaned by rinsing in a fluid, drying with a gas, and baking at a temperature for a time period. In some embodiments, the fluid may include IPA. Moreover, in some embodiments, the gas may include nitrogen. Further, in some embodiments, the temperature may be 90° C. Further still, in some embodiments, the time period may be 2 minutes.

Further, the partially-fabricated device 300a may be plasma cleaned before applying the adhesion promoter to a surface of the sacrificial layer 304. The partially-fabricated device 300a may be plasma cleaned in a variety of ways. For example, the partially-fabricated device 300a may be plasma cleaned at a power for a time period. In some embodiments, the power may be high. Moreover, in some embodiments, the time period may be 5 minutes.

Moreover, a surface of the sacrificial layer 304 may be treated, such that the first bio-compatible layer 310 bonds to the treated surface during formation of the first bio-compatible layer 310. For example, the surface 308 of the sacrificial layer 304 may be treated, such that the first bio-compatible layer 310 bonds to the treated surface during formation of the first bio-compatible layer 310. With this arrangement, the surface 308 may be roughened, such that adhesion of the first bio-compatible layer 310 to the sacrificial layer 304 may be improved.

The surface 308 may be treated in a variety of ways. For example, the surface 308 of the sacrificial layer 304 may be treated by etching using an inductively coupled plasma at a power for a time. In some embodiments, the inductively coupled plasma may include an oxygen plasma. Moreover, in some embodiments, the power may be 400 Watts (W) with a 300 W bias. Further, in some embodiments, the time period may be 1 to 3 minutes. In some examples, the inductively coupled plasma may unevenly etch the surface 308, such that the surface 308 may be roughened. Other plasmas and/or types of plasmas may be used as well, such as plasma asher, a reactive ion etcher, etc.

Next, a seed layer 314 is formed over the first bio-compatible layer 310 to provide a partially-fabricated device 300c, as shown in FIG. 3c. Such a seed layer 314 can be used to adhere to both the first bio-compatible layer 310, and any additional metal structure that is patterned over the seed layer 314, as will be described below. For example, the seed layer 314 may include one or more materials that both adheres well to the first bio-compatible layer 310 and serves as a guide to electroplate the remainder of a metal structure that forms a component. In such an example, the seed layer 314 may include palladium, titanium, and/or gold. In some embodiments, the seed layer 314 may include a palladium layer and a gold layer. In some embodiments, the seed layer 314 may include a titanium layer and a gold layer.

Moreover, the seed layer 314 may have a variety of thicknesses. For example, a palladium layer of the seed layer 314 may have a thickness between 20 to 30 nanometers, such as 30 nanometers. Moreover, a titanium layer of the seed layer 314 may have a thickness between 20 to 30 nanometers, such as 30 nanometers. Further, a gold layer of the seed layer 314 may have a thickness of 100 nanometers. Other thicknesses of the seed layer 314 are possible as well.

In an example, the seed layer 314 may be formed by a microfabrication process such as evaporation. However, in other examples, the seed layer 314 may be formed by other microfabrication processes, such as sputtering. In some embodiments, a palladium layer of the seed layer 314 may be formed over the first bio-compatible layer 310, and a gold layer of the seed layer 314 may be formed over the palladium layer of the seed layer 314. In some embodiments, a titanium layer of the seed layer 314 may be formed over the first bio-compatible layer 310, and a gold layer of the seed layer 314 may be formed over the titanium layer of the seed layer 314.

Moreover, the partially-fabricated device 300b may be cleaned before forming the seed layer 314 over the first bio-compatible layer 310. The partially-fabricated device 300b may be cleaned in a variety of ways. For example, the partially-fabricated device 300b may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further, the partially-fabricated device 300b may be baked before forming the seed layer 314 over the first bio-compatible layer 310. The partially-fabricated device 300b may be baked at a temperature for a time period. In some embodiments, the temperature may be 90° C. Moreover, in some embodiments, the time period may be 5 minutes. Further, in some embodiments, the partially-fabricated device 300b may be baked on a hot plate. After the partially-fabricated device 300b is baked, the partially-fabricated device 300b may be cooled to room temperature.

Further still, the partially-fabricated device 300b may be plasma cleaned before forming the seed layer 314 over the first bio-compatible layer 310. With this arrangement, a surface 311 of the first bio-compatible layer 310 (as shown in FIG. 3b) may be roughened, such that adhesion of the seed layer 314 to the first bio-compatible layer 310 may be improved. The partially-fabricated device 300b may be plasma cleaned in a variety of ways. For example, the partially-fabricated device 300b may be plasma cleaned at a power for a time period. In some embodiments, the power may be high. Moreover, in some embodiments, the time period may be 5 minutes.

In another example, the surface 311 of the first bio-compatible layer may treated before forming the seed layer 314. With this arrangement, the surface 311 of the first bio-compatible layer 310 may be roughened, such that adhesion of the seed layer 314 to the first bio-compatible layer 310 may be improved. The surface 311 may be treated in a variety of ways. For example, the surface 311 of the first bio-compatible layer 310 may be treated by etching using an inductively coupled plasma at a power for a time. In some embodiments, the inductively coupled plasma may include an oxygen plasma. Moreover, in some embodiments, the power may be 400 W with a 300 W bias. In some examples, the inductively coupled plasma may unevenly etch the surface 311, such that the surface 311 may be roughened. Further, in some embodiments, the time period may be 1 to 3 minutes. Other plasmas and/or types of plasmas may be used as well, such as plasma asher, a reactive ion etcher, etc.

As shown in FIG. 3d, a first mask 316 is formed over a portion 318 of the seed layer 314 to provide a partially-fabricated device 300d. The first mask 316 may include a variety of materials. For example, the first mask 316 may include a photoresist layer, such as a photoresist layer comprising 2-ethoxyethyl acetate. In such an example, the first mask 316 may be AZ4620® sold by Capital Scientific.

Moreover, the first mask 316 may have a variety of thicknesses. For example, the first mask 316 may have thicknesses of 5 micrometers. Other thicknesses of the first mask 316 are possible as well.

In an example, the first mask 316 may be formed over the portion 318 of the first bio-compatible layer 310 by spin coating and patterning.

The first mask 316 may be spin coated in a variety of ways. For example, a material may be spin coated by placing the material on the partially-fabricated device 300c, applying a spread cycle, applying a spin cycle, and applying a deceleration cycle.

In some embodiments, placing the material on the partially-fabricated device 300c may include pouring (or pipetting) the material onto the partially-fabricated device 300c.

Moreover, in some embodiments, applying the spread cycle may include rotating the partially-fabricated device 300c at a first rate for a first time period. And in such embodiments, the first rate may be 500 rpm. And in such embodiments, the first time period may be 8 seconds. With this arrangement, the material may be spread over the seed layer 314. The spread cycle may further include accelerating the partially-fabricated device 300c at a second rate for a second time period before rotating the partially-fabricated device 300c at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300c at a first rate for a first time period. And in such embodiments, the first rate may be 3000 rpm. And in such embodiments, the first time period may be 28 to 38 seconds. With this arrangement, the thickness of the first mask 316 may be formed. The spin cycle may further include accelerating the partially-fabricated device 300c at a second rate for a second time period before rotating the partially-fabricated device 300c at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300c at a rate for a time period. And in such embodiments, the rate may be 1500 rpm per second. And in such embodiments, the time period may be 2 seconds.

Moreover, in some embodiments, the partially-fabricated device 300c may be placed in a vacuum chuck before placing the material on the partially-fabricated device 300c.

And in such embodiments, the partially-fabricated device 300c may be removed from the vacuum chuck after applying the declaration cycle.

After the first mask 316 is spin coated, the first mask 316 may be baked before patterning. The first mask 316 may be baked in a variety of ways. For example, the first mask 316 may be baked at a temperature for a time period. In some embodiments, the temperature may be 90° C. Moreover, in some embodiments, the time period may be 2 minutes. After the first mask 316 is baked, the first mask 316 may be cooled to room temperature.

In addition, the first mask 316 may be patterned in a variety of ways. For example, a material may be patterned by exposing and developing. In such an example, the material may be exposed to light at an intensity for a first time period, and developed by soaking in a fluid for a second time period. In some embodiments, the light may be ultra violet light (UV light) that is generated by a mercury lamp. Moreover, in some embodiments, the intensity may be 16 to 19 milliwatts per centimeter (mW/cm$^2$). Further, in some embodiments, the first time period may be 10 to 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 1 minute.

Moreover, the partially-fabricated device 300d may be further processed after formation of the first mask 316 over the portion 318 of the seed layer 314. The partially-fabricated device 300d may be further processed in a variety of ways. For example, the partially-fabricated device 300d may be further processed by rinsing in a fluid, blow drying with a gas, and baking at a temperature for a time period. In some embodiments, the fluid may include DI water. Moreover, in some embodiments, the gas may include nitrogen. Further, in some embodiments, the temperature may be 90° C. Further still, in some embodiments, the time period may be 30 minutes. After the first mask 316 is further processed after formation of the first mask 316 over the portion 318 of the seed layer 314, the first mask 316 may be cooled to room temperature.

Further, the partially-fabricated device 300c may be cleaned before forming the first mask 316 over the portion 318 of the seed layer 314. The partially-fabricated device 300c may be cleaned in a variety of ways. For example, the partially-fabricated device 300c may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300c may be baked before forming the first mask 316 over the portion 318 of the seed layer 314. The partially-fabricated device 300c may be baked at a temperature for a time period. In some embodiments, the temperature may be 90° C. Moreover, in some embodiments, the time period may be 2 minutes. Further, in some embodiments, the partially-fabricated device 300c may be baked on a hot plate. After the partially-fabricated device 300c is baked, the partially-fabricated device 300c may be cooled to room temperature.

As shown in FIG. 3e, a first metal layer 320 is formed over exposed portions 328 of the seed layer 314 (i.e., the portions that are not covered by the first mask 316) to provide a partially-fabricated device 300e. The first metal layer 320 defines components including an antenna 322, electrical contacts 324, and electrical interconnects 326.

The first metal layer 320 may include a variety of conductive materials. For example, the first metal layer 320 may include one or more layers of platinum, silver, gold, palladium, titanium, copper, chromium, nickel, aluminum, other metals or conductive materials, and combinations thereof. In some embodiments, the first metal layer 320 may include a substantially transparent conductive material for at least some components (e.g., a material such as indium tin oxide). In an example, the first metal layer 320 may comprise one layer of gold.

Moreover, the first metal layer 320 may have a variety of thicknesses. For example, the first metal layer 320 may have a thickness between 6 to 10 micrometers, such as between 6 to 7 micrometers, 7 to 8 micrometers, or 9 to 10 micrometers. Other thicknesses of the first metal layer 320 are possible as well.

In an example, the first metal layer 320 may be formed by a microfabrication process such as electroplating. Other microfabrication processes for forming the first metal layer 320 are possible as well. The first metal layer 320 may be electroplated in a variety of ways. For example, the first metal layer 320 may be electroplated in a bath at a current for a time period. In some embodiments, the current is 60 milliamps (mA). Moreover, in some embodiments, the time period is 60 to 75 minutes.

Moreover, the partially-fabricated device 300*d* may be plasma cleaned before forming the first metal layer 320 over the exposed portions 328 of the seed layer 314. The partially-fabricated device 300*d* may be plasma cleaned in a variety of ways. For example, the partially-fabricated device 300*d* may be plasma cleaned at a power for a time period. In some embodiments, the power may be high. Moreover, in some embodiments, the time period may be 5 minutes.

Next, the first mask 316 is removed and a second mask 329 is formed over the first metal layer 320 to provide a partially-fabricated device 300*f*, as shown in FIG. 3*f*.

The first mask 316 may be removed in a variety of ways. For example, the first mask 316 may be removed by soaking in a first fluid for a time period, rinsing in a second fluid, and drying with a gas. In some embodiments, the first fluid may include a solvent, such as acetone. Moreover, in some embodiments, the time period may be 2 minutes. Further, in some embodiments, the second fluid may include IPA. Further still, in some embodiments, the gas may include nitrogen. And, in an example, removal may further involve agitation during soaking in the first fluid. As another example, the first mask 316 may be removed using an inductively coupled plasma, such as oxygen plasma.

The second mask 329 may include a variety of materials. For example, the second mask 329 may include one or more photoresist layers, such as one photoresist layer comprising 2-ethoxyethyl acetate. In such an example, the second mask 329 may be AZ4620® sold by Capital Scientific. In another example, the second mask 329 may include one photoresist layer comprising 1-methoxy-2-propanol acetate. In such an example, the second mask 329 may be AZ nLOF 2070® sold by AZ Electronic Materials. In yet another example, the second mask 329 may include one photoresist layer comprising cyclohexanone. In such an example, the second mask 329 may be NR9-3000PY sold by Futurrex, Inc.

Moreover, the second mask 329 may have a variety of thicknesses. For example, the second mask 329 may have a thickness of 5 micrometers. Other thicknesses of the second mask 329 are possible as well.

In an example, the second mask 329 may be formed over the first metal layer 320 by spin coating and patterning.

The second mask 329 may be spin coated in a variety of ways. For example, a material may be spin coated by placing the material on the partially-fabricated device 300*e* (after the first mask 316 has been removed), applying a spread cycle, applying a spin cycle, and applying a deceleration cycle.

In some embodiments, placing the material on the partially-fabricated device 300*e* may include pouring (or pipetting) the material onto the partially-fabricated device 300*e*.

Moreover, in some embodiments, applying the spread cycle may include rotating the partially-fabricated device 300*e* at a first rate for a first time period. And in such embodiments, the first rate may be 500 rpm. And in such embodiments, the first time period may be 8 seconds. With this arrangement, the material may be spread over the partially-fabricated device 300*e*. The spread cycle may further include accelerating the partially-fabricated device 300*e* at a second rate for a second time period before rotating the partially-fabricated device 300*e* at the first rate for the first time period. In some embodiments, the second rate may be 250 rpm. Moreover, in some embodiments, the second time period may be 2 seconds.

Further, in some embodiments, applying the spin cycle may include rotating the partially-fabricated device 300*e* at a first rate for a first time period. And in such embodiments, the first rate may be 3000 rpm. And in such embodiments, the first time period may be 28 to 38 seconds. With this arrangement, the thickness of the second mask 329 may be formed. The spin cycle may further include accelerating the partially-fabricated device 300*e* at a second rate for a second time period before rotating the partially-fabricated device 300*e* at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300*e* at a rate for a time period. And in such embodiments, the rate may be 1500 rpm per second. And in such embodiments, the time period may be 2 seconds.

Moreover, in some embodiments, the partially-fabricated device 300*e* may be placed in a vacuum chuck before placing the material on the partially-fabricated device 300*e*. And in such embodiments, the partially-fabricated device 300*e* may be removed from the vacuum chuck after applying the deceleration cycle.

After the second mask 329 is spin coated, the second mask 329 may be baked before patterning. The second mask 329 may be baked in a variety of ways. For example, the second mask 329 may be baked at a temperature for a time period. In some embodiments, the temperature may be 90° C. Moreover, in some embodiments, the time period may be 2 minutes. After the second mask 329 is baked, the second mask 329 may be cooled to room temperature.

In addition, the second mask 329 may be patterned in a variety of ways. For example, the material may be patterned by exposing and developing. In such an example, the material may be exposed to light at an intensity for a first time period, and developed by soaking in a fluid for a second time period. In some embodiments, the light may be ultra violet light (UV light) that is generated by a mercury lamp. Moreover, in some embodiments, the intensity may be 16 to 19 mW/cm$^2$. Further, in some embodiments, the first time period may be 10 to 12 seconds. Moreover, in some embodiments, the fluid may comprise four parts DI and one part a fluid comprising potassium borates. And in such embodiments, the fluid comprising potassium borates may be AZ® 400K Developer sold by AZ Electronics Materials. Further still, in some embodiments, the second time period may be about 1 minute.

Moreover, the partially-fabricated device 300f may be further processed after formation of the second mask 329 over the first metal layer 320. The partially-fabricated device 300f may be further processed in a variety of ways. For example, the partially-fabricated device 300f may be further processed by rinsing in a fluid, blow drying with a gas, and baking at a temperature for a time period. In some embodiments, the fluid may include DI water. Moreover, in some embodiments, the gas may include nitrogen. Further, in some embodiments, the temperature may be 90° C. Further still, in some embodiments, the time period may be 30 minutes. After the second mask 329 is processed after formation, the second mask 329 may be cooled to room temperature.

Further, the partially-fabricated device 300e (after the first mask 316 has been removed) may be cleaned before forming the second mask 329 over the first metal layer 320. The partially-fabricated device 300e may be cleaned in a variety of ways. For example, the partially-fabricated device 300e may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300e (after the first mask 316 has been removed) may be baked before forming the second mask 329 over the first metal layer 320. The partially-fabricated device 300e may be baked at a temperature for a time period. In some embodiments, the temperature may be 90° C. Moreover, in some embodiments, the time period may be 2 minutes. Further, in some embodiments, the partially-fabricated device 300e may be baked on a hot plate. After the partially-fabricated device 300e is baked, the partially-fabricated device 300e may be cooled to room temperature.

As shown in FIG. 3g, the portion 318 of the seed layer 314 is removed and the second mask 329 is removed to provide a partially-fabricated device 300g. In some embodiments, a gold layer of the portion 318 of the seed layer 314 and/or a palladium layer of the portion 318 of the seed layer 314 may be removed.

The portion 318 of the seed layer 314 may be removed in a variety of ways. For example, the portion 318 of the seed layer 314 may be removed by wet etching. The gold layer of the portion 318 of the seed layer 314 may be wet etched in a variety of ways. For example, the gold layer of the portion 318 of the seed layer 314 may be wet etched for a time period at a temperature. In some embodiments, the time period may be between 1 to 2 minutes. Moreover, in some embodiments, the temperature may be room temperature. And, in some embodiments, removing the gold layer of the portion 318 of the seed layer 314 may involve agitation (e.g., constant agitation) during wet etching. After the gold layer of the portion 318 of the seed layer 314 is wet etched, removing the gold layer of the portion 318 of the seed layer 314 may involve rinsing in a fluid and drying with a gas. In some embodiments, the fluid may include DI water. Moreover, in some embodiments, the gas may include nitrogen.

Moreover, the palladium layer of the portion 318 of the seed layer 314 may be wet etched in a variety of ways. For example, the palladium layer of the portion 318 of the seed layer 314 may be wet etched for a time period at a temperature. In some embodiments, the time period may be 30 seconds. Moreover, in some embodiments, the temperature may be 70° C. After the palladium layer of the portion 318 of the seed layer 314 is wet etched, removing the palladium layer of the portion 318 of the seed layer 314 may involve rinsing in a fluid and drying with a gas. In some embodiments, the fluid may include DI water. Moreover, in some embodiments, the gas may include nitrogen.

The second mask 329 may be removed in a variety of ways. For example, the second mask 329 may be removed by soaking in a first fluid for a time period, rinsing in a second fluid, and drying with a gas. In some embodiments, the first fluid may include a solvent, such as acetone. Moreover, in some embodiments, the time period may be 2 minutes. Further, in some embodiments, the second fluid may include IPA. Further still, in some embodiments, the gas may include nitrogen. And, in an example, removal may further involve agitation during soaking in the first fluid. As another example, the second mask 329 may be removed using an inductively coupled plasma, such as an oxygen plasma.

As shown in FIG. 3h, a third mask 330 is formed over a portion 332 of the first bio-compatible layer 310 and a portion 334 the first metal layer 320 to provide a partially-fabricated device 300h. The third mask 330 may include a variety of materials. For example, the third mask 330 may include one or more photoresist layers, such as one photoresist layer comprising 2-ethoxyethyl acetate. In such an example, the third mask 330 may be AZ4620® sold by Capital Scientific. In another example, the third mask 330 may include one photoresist layer comprising 1-methoxy-2-propanol acetate. In such an example, the third mask 330 may be AZ nLOF 2070® sold by AZ Electronic Materials. In yet another example, the third mask 330 may include one photoresist layer comprising cyclohexanone. In such an example, the third mask 330 may be NR9-3000PY sold by Futurrex, Inc.

Moreover, the third mask 330 may have a variety of thicknesses. For example, the third mask 330 may have a thicknesses of 5 micrometers. Other thicknesses of the third mask 330 are possible as well.

In an example, the third mask 330 may be formed over the portion 332 of the first bio-compatible layer 310 and the portion 334 of the first metal layer 320 by spin coating and patterning.

The third mask 330 may be spin coated in a variety of ways. For example, a material may be spin coated by placing the material on the partially-fabricated device 300g, applying a spread cycle, applying a spin cycle, and applying a deceleration cycle.

In some embodiments, placing the material on the partially-fabricated device 300g may include pouring (or pipetting) the material onto the partially-fabricated device 300g.

Moreover, in some embodiments, applying the spread cycle may include rotating the partially-fabricated device 300g at a first rate for a first time period. And in such embodiments, the first rate may be 500 rpm. And in such embodiments, the first time period may be 8 seconds. With this arrangement, the material may be spread over the partially-fabricated device 300g. The spread cycle may further include accelerating the partially-fabricated device 300g at a second rate for a second time period before rotating the partially-fabricated device 300g at the first rate for the first time period. In some embodiments, the second rate may be 250 rpm. Moreover, in some embodiments, the second time period may be 2 seconds.

Further, in some embodiments, applying the spin cycle may include rotating the partially-fabricated device 300g at a first rate for a first time period. And in such embodiments, the first rate may be 3000 rpm. And in such embodiments, the first time period may be 28 to 38 seconds. With this arrangement, the thickness of the third mask 330 may be formed. The spin cycle may further include accelerating the partially-fabricated device 300g at a second rate for a second time period before rotating the partially-fabricated device 300g at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300g at a rate for a time period. And in such embodiments, the rate may be 1500 rpm per second. And in such embodiments, the time period may be 2 seconds.

Moreover, in some embodiments, the partially-fabricated device 300g may be placed in a vacuum chuck before placing the material on the partially-fabricated device 300g. And in such embodiments, the partially-fabricated device 300g may be removed from the vacuum chuck after applying the deceleration cycle.

After the third mask 330 is spin coated, the third mask 330 may be baked before patterning. The third mask 330 may be baked in a variety of ways. For example, the third mask 330 may be baked at a temperature for a time period. In some embodiments, the temperature may be 90° C. Moreover, in some embodiments, the time period may be 2 minutes. After the third mask 330 is baked, the third mask 330 may be cooled to room temperature.

In addition, the third mask 330 may be patterned in a variety of ways. For example, the material may be patterned by exposing and developing. In such an example, the material may be exposed to light at an intensity for a first time period, and developed by soaking in a fluid for a second time period. In some embodiments, the light may be ultra violet light (UV light) that is generated by a mercury lamp. Moreover, in some embodiments, the intensity may be the intensity may be 16 to 19 mW/cm$^2$. Further, in some embodiments, the first time period may be 10 to 12 seconds. Moreover, in some embodiments, the fluid may comprise four parts DI and one part a fluid comprising potassium borates. And in such embodiments, the fluid comprising potassium borates may be AZ® 400K Developer sold by AZ Electronics Materials. Further still, in some embodiments, the second time period may be about 1 minute.

Moreover, the partially-fabricated device 300h may be further processed after formation of the third mask 330 over the portion 332 of the first bio-compatible layer 310 and the portion 334 the first metal layer 320. The partially-fabricated device 300h may be further processed in a variety of ways. For example, the partially-fabricated device 300h may be further processed by rinsing in a fluid, blow drying with a gas, and baking at a temperature for a time period. In some embodiments, the fluid may include DI water. Moreover, in some embodiments, the gas may include nitrogen. Further, in some embodiments, the temperature may be 90° C. Further still, in some embodiments, the time period may be 30 minutes. After the third mask 330 is processed after formation, the third mask 330 may be cooled to room temperature.

Further, the partially-fabricated device 300g may be cleaned before forming the third mask 330 over the portion 332 of the first bio-compatible layer 310 and the portion 334 of the first metal layer 320. The partially-fabricated device 300g may be cleaned in a variety of ways. For example, the partially-fabricated device 300g may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300g may be baked before forming the third mask 330 over the portion 332 of the first bio-compatible layer 310 and the portion 334 of the first metal layer 320. The partially-fabricated device 300g may be baked at a temperature for a time period. In some embodiments, the temperature may be 90° C. Moreover, in some embodiments, the time period may be 2 minutes. Further, in some embodiments, the partially-fabricated device 300g may be baked on a hot plate. After the partially-fabricated device 300g is baked, the partially-fabricated device 300g may be cooled to room temperature.

As shown in FIG. 3i, a second metal layer 336 is formed over exposed portions 344 of the first bio-compatible layer 310 and exposed portions 346 of the first metal layer 320 (i.e., the portions that are not covered by the third mask 330) to provide a partially-fabricated device 300i. The second metal layer 336 defines electrical interconnects 338 and sensor electrodes 340.

The second metal layer 336 may include a variety of conductive materials. In one example, the second metal layer 336 may include a first conductive layer and a second conductive layer. The first conductive layer may be provided on exposed portions 344 of the first bio-compatible layer and exposed portions 346 of the first metal layer 320. The second conductive layer may be provided over at least a portion of the first conductive layer that is formed on exposed surfaces 344 of the bio-compatible device. The second conductive layer may also be provided over a portion of the first conductive layer that is provided on exposed portions 346 of the first metal layer 320.

The first conductive layer may comprise a first metal, and the second metal layer may comprise a second metal. The first metal may be chosen so that the first conductive layer provides a continuous electrical pathway to and from the sensor electrodes 340, and the second metal may be chosen to provide a surface for either oxidation or reduction reactions at the sensor electrodes 440. Depending on the application, the second metal may be prone to cracking during subsequent steps in the fabrication process. To provide a continuous electrical pathway to and from the sensor electrodes, the first metal may be more malleable and less prone to cracking during subsequent fabrications than the second metal.

For instance, if the bio-compatible device is used in an eye-mounted device and glucose is the measured analyte, the second metal may be platinum, and the first metal may be a metal that is more malleable than platinum, such as gold. Alternatively, the second metal may be a different metal, such as copper or silver.

Additionally, the second metal layer 336 may comprise a third conductive layer of a third metal that is between the first conductive layer and the second conductive layer. The third conductive layer may provide additional structure for the sensor electrodes 340. The third metal could be, for example, palladium.

The third conductive layer may be formed in a variety of ways. In one example, the third conductive layer may be formed over the first conductive layer. Alternatively, the third conductive layer may be formed over the portion of the first conductive layer that is formed on exposed surfaces 344 of the bio-compatible device. In either example, the second conductive layer may be formed over the third conductive layer.

Moreover, each layer in the second metal layer 336 may have a variety of thicknesses. For example, the first conductive layer of the second metal layer 336 may have a thickness between 100 nm to 10 microns, such as about 250 nm, and the second conductive layer may have thickness between about 50 to about 300 nanometers, such as about 100 or about 120 nanometers. In examples in which the second metal layer 336 comprises a third conductive layer, the third conductive layer may have a thickness between 10 to 50 nanometers, such as 30 nanometers. Other thicknesses of the second metal layer 336 are possible as well.

In an example, the second metal layer 336 may be formed by a microfabrication process such as sputtering. However, in other examples, the second metal layer 336 may be formed by other microfabrication processes such as evaporation.

Moreover, the partially-fabricated device 300h may be plasma cleaned before forming the second metal layer 336 over the exposed portions 344 of the first bio-compatible layer 310 and the exposed portions 346 of the first metal layer 320. The partially-fabricated device 300h may be plasma cleaned in a variety of ways. For example, the partially-fabricated device 300h may be plasma cleaned at a power for a time period. In some embodiments, the power may be high. Moreover, in some embodiments, the time period may be 60 seconds.

Next, the third mask 330 is removed to provide a partially-fabricated device 300j, as shown in FIG. 3j. The third mask 330 may be removed in a variety of ways. For example, the third mask 330 may be removed by soaking in a first fluid for a first time period, rinsing in a second fluid, drying with a gas, and baking at a temperature for a second time period. In some embodiments, the first fluid may include a solvent, such as acetone. Moreover, in some embodiments, the first time period may be 1 to 5 hours, such as 1 to 2 hours or 4 to 5 hours. Further, in some embodiments, the second fluid may include IPA. Further still, in some embodiments, the gas may include nitrogen. Moreover, in some embodiments, the temperature may be 90° C. Further, in some embodiments, the second time period may be 5 minutes. And, in an example, removal may further involve sonication for a time period (e.g., 2 to 3 seconds) after soaking in the first fluid. For instance, in some embodiments, removal may involve sonication for the time period after soaking in the first fluid for 1 hour. As another example, the third mask 330 may be removed using an inductively coupled plasma, such as an oxygen plasma.

After the third mask 330 is removed, the partially-fabricated device 300j may be rinsed in a fluid, dried with a gas, and baked at a temperature for a time period. In some embodiments, the fluid may include IPA. Moreover, in some embodiments, the gas may include nitrogen. Further, in some embodiments, the temperature may be 90° C. Further still, in some embodiments, the time period may be 5 minutes.

Together, the first metal layer 320 and the second metal layer 336 are a conductive pattern 342. The conductive pattern 342 defines the antenna 322, the electrical contacts 324, the electrical interconnects 326, the electrical interconnects 338, and the sensor electrodes 340.

As shown in FIG. 3k, a protective layer 348 is formed over the sensor electrodes 340 to provide a partially-fabricated device 300k. The protective layer 348 may include a variety of materials. For example, the protective layer 348 may include one or more photoresist layers, such as one photoresist layer comprising 2-ethoxyethyl acetate. In such an example, the protective layer 348 may be AZ6420® sold by Capital Scientific. However, in other examples, the protective layer 348 may include one or more layers of metal, such as aluminum.

Moreover, the protective layer 348 may have a variety of thicknesses. For example, the protective layer 348 may have a thickness of 40 micrometers. Other thicknesses of the protective layer 348 are possible as well.

In an example, the protective layer 348 may be formed over the sensor electrodes 340 by spin coating and patterning. However, in other examples, the protective layer 348 may be formed by microfabrication processes such as evaporation and/or sputtering.

The protective layer 348 may be spin coated in a variety of ways. For example, the protective layer 348 may be spin coated in steps. In such an example, a first step may involve placing a first material on the partially-fabricated device 300j, applying a spread cycle, applying a spin cycle, and applying a deceleration cycle.

In some embodiments, placing the first material on the partially-fabricated device 300j may include pouring (or pipetting) the first material onto the partially-fabricated device 300j.

Moreover, in some embodiments, applying the spread cycle may include rotating the partially-fabricated device 300j at a first rate for a first time period. And in such embodiments, the first rate may be 500 rpm. And in such embodiments, the first time period may be 5 to 8 seconds. With this arrangement, the first material may be spread over the sensor electrodes 340. The spread cycle may further include accelerating the partially-fabricated device 300j at a second rate for a second time period before rotating the partially-fabricated device 300j at the first rate for the first time period. In some embodiments, the second rate may be 100 to 250 rpm per second. Moreover, in some embodiments, the second time period may be 2 to 5 seconds.

Further, in some embodiments, applying the spin cycle may include rotating the partially-fabricated device 300j at a first rate for a first time period. And in such embodiments, the first rate may be 900 to 1000 rpm. And in such embodiments, the first time period may be 38 to 118 seconds. With this arrangement, a first portion of the thickness of the protective layer 348 may be formed. The spin cycle may further include accelerating the partially-fabricated device 300j at a second rate for a second time period before rotating the partially-fabricated device 300j at the first rate for the first time period. In some embodiments, the second rate may be 450 to 500 rpm per second. Moreover, in some embodiments, the second time period may be 2 seconds.

Further still, in some embodiments, applying deceleration cycle comprises decelerating the partially-fabricated device 300j at a rate for a time period. And in such embodiments, the rate may be 450 to 500 rpm per second. And in such embodiments, the time period may be 2 seconds.

Moreover, in some embodiments, the partially-fabricated device 300j may be placed in a vacuum chuck before placing the first material on the partially-fabricated device 300j.

After the first step, the first material may be baked at a temperature for a time period. In some embodiments, the temperature may be 90° C. Moreover, in some embodiments, the time period may be 1 minute.

In such an example, a second step may involve placing a second material on the first material, applying a spread cycle, applying a spin cycle, and applying a deceleration cycle.

In some embodiments, placing the second material on the first material may include pouring (or pipetting) the second material onto the first material.

Moreover, in some embodiments, applying the spread cycle may include rotating the partially-fabricated device 300*j* at a first rate for a first time period. And in such embodiments, the first rate may be 500 rpm. And in such embodiments, the first time period may be 5 to 8 seconds. With this arrangement, the second material may be spread over the first material. The spread cycle may further include accelerating the partially-fabricated device 300*j* at a second rate for a second time period before rotating the partially-fabricated device 300*j* at the first rate for the first time period. In some embodiments, the second rate may be 100 to 250 rpm per second. Moreover, in some embodiments, the second time period may be 2 to 5 seconds.

Further, in some embodiments, applying the spin cycle may include rotating the partially-fabricated device 300*j* at a first rate for a first time period. And in such embodiments, the first rate may be 900 to 1000 rpm. And in such embodiments, the first time period may be 38 to 118 seconds. With this arrangement, a second portion of the thickness of the protective layer 348 may be formed. The spin cycle may further include accelerating the partially-fabricated device 300*j* at a second rate for a second time period before rotating the partially-fabricated device 300*j* at the first rate for the first time period. In some embodiments, the second rate may be 450 to 500 rpm per second. Moreover, in some embodiments, the second time period may be 2 seconds.

Further still, in some embodiments, applying deceleration cycle comprises decelerating the partially-fabricated device 300*j* at a rate for a time period. And in such embodiments, the rate may be 450 to 500 rpm per second. And in such embodiments, the time period may be 2 seconds.

And in some embodiments, the partially-fabricated device 300*j* may be removed from the vacuum chuck after applying the deceleration cycle.

After the second step, the first and second material may be baked at a temperature for a time period. In some embodiments, the temperature may be 90° C. Moreover, in some embodiments, the time period may be 10 minutes. And such an example may further involve baking the first and second materials until room temperature at a rate. In some embodiments, the rate may be 2° C. per minute.

In addition, the protective layer 348 may be patterned in a variety of ways. For example, the first and second material may be patterned by exposing and developing. And, in such an example, the first and second material may be exposed and developed in steps.

In such an example, a first step may involve exposing the first and second material to light at an intensity for a first time period. In some embodiments, the light may be ultraviolet light (UV light) that may be generated by a mercury lamp. Moreover, in some embodiments, the intensity may be the intensity may be 16 to 19 mW/cm$^2$. Further, in some embodiments, the first time period may be 26 seconds. Moreover, in such an example, a second step may involve repeating the first step. In another example, the first time period may include one or more cycles (e.g., 4 cycles) where each of the one or more cycles includes an exposure time period (e.g., 20 seconds) and waiting time period (e.g., 30 seconds to 2 minutes).

Further, in such an example, a third step may involve developing the first and second material by soaking in a fluid for a second time period. In some embodiments, the fluid may comprise four parts DI and one part a fluid comprising potassium borates. And in such embodiments, the fluid comprising potassium borates may be AZ® 400K Developer sold by AZ Electronics Materials. Moreover, in some embodiments, the second time period may be 4 minutes. Further still, in such an example, a fourth step may involve repeating the third step.

Moreover, the partially-fabricated device 300*k* may be further processed after formation of the protective layer 348 over the sensor electrodes 340. The protective layer 348 may be further processed in a variety of ways. For example, the protective layer 348 may be further processed by rinsing in a fluid and drying with a gas. In some embodiments, the fluid may include DI water. Moreover, in some embodiments, the gas may include nitrogen.

In such an example, the partially-fabricated device 300*k* may then baked at a temperature for a time period. In some embodiments, the temperature may be 90° C. Moreover, in some embodiments, the time period may be 20 minutes.

Further, the partially-fabricated device 300*j* may be cleaned before forming the protective layer 348 over the sensor electrodes 340. The partially-fabricated device 300*j* may be cleaned in a variety of ways. For example, the partially-fabricated device 300*j* may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300*j* may be baked before forming the protective layer 348 over the sensor electrodes 340. The partially-fabricated device 300*j* may be baked at a temperature for a time period. In some embodiments, the temperature may be 90° C. Moreover, in some embodiments, the time period may be 5 minutes. Further, in some embodiments, the partially-fabricated device 300*i* may be baked on a hot plate. After the partially-fabricated device 300*j* is baked, the partially-fabricated device 300*j* may be cooled to room temperature.

Next, an electronic component 350 is mounted to the electrical contacts 324 to provide a partially-fabricated device 300*l*, as shown in FIG. 31. The electronic component 350 could include, for example, one or more integrated circuits (ICs) and/or one or more discrete electronic components. Heat, pressure, a pick-and-place tool and a bonding medium (anisotropic conductive paste (ACP), anisotropic conductive film (ACF), solder and flux, solder paste, solder followed by underfill, etc.), or a flip-chip bonder, for example, may be used to adhere a first surface 352 of the electronic component 350 to the electrical contacts 324. The electronic component 350 has a second surface 354 opposite the first surface 352.

As shown in FIG. 3*m*, a surface 356 of the first bio-compatible layer 310 is treated to provide a partially-fabricated device 300*m*, such that a surface of another bio-compatible layer, such as a second bio-compatible layer, bonds to the surface during formation of the other bio-compatible layer. The surface 356 of the first bio-compatible layer 310 may be treated in a variety of ways. For example, the surface 356 of the first bio-compatible layer 310 may be treated by etching using an inductively coupled plasma at a power for a time period. With this arrangement, the surface 356 of the first bio-compatible layer 310 may be roughened. In some embodiments, the inductively coupled plasma may include an oxygen plasma. Moreover, in some embodiments, the power may be 400 W with a 300 W bias. Further, in some embodiments, the time period may be 1 minute. In some examples, the inductively coupled plasma may unevenly etch the surface 356, such that the surface 356 may be roughened. Other plasmas and/or types of plasmas may be used as well, such as a plasma asher, a reactive ion etcher, etc.

The partially-fabricated device 300*l* may be baked at a temperature for a time period before treating the surface 356 of the first bio-compatible layer 310. In some embodiments, the temperature may be 90° C. Moreover, in some embodiments, the time period may be 1 hour.

As shown in FIG. 3*n*, a second bio-compatible layer 358 is formed over the first bio-compatible layer 310, the electronic component 350, the antenna 322, the electrical interconnects 338, the protective layer 348, the electrical contacts 324, and the electrical interconnects 326 to provide a partially-fabricated device 300*n*. The second bio-compatible layer 358 defines a second side 360 of the bio-compatible device. That is, the second bio-compatible layer 358 defines an outer edge of the bio-compatible device.

In an example, the second bio-compatible layer 358 can be composed of the same polymeric material as the first bio-compatible layer 310. However, in other examples, the second bio-compatible layer 358 can be composed of a different polymeric material than the first bio-compatible 310. The second bio-compatible layer 358 can be any one of the polymeric materials mentioned herein that is both bio-compatible and electrically insulating. The second bio-compatible layer 358 thus serves to seal and insulate the components.

Moreover, the second bio-compatible layer 358 may have a variety of thicknesses. For example, the second bio-compatible layer 358 may have a thickness between one or more embedded components and a surface of the second bio-compatible layer 358 between 5 to 100 micrometers, such as 15 micrometers. Other thicknesses for the second bio-compatible layer 358 are possible as well.

In an example, the second bio-compatible layer 358 may be formed the same or similar way as the first bio-compatible layer 310 may be formed. However, in other examples, the second bio-compatible layer 358 may be formed by a different process (or processes) than the process (or processes) used to form the first bio-compatible layer 310.

For example, the second bio-compatible layer 358 may be formed by a microfabrication process such as chemical vapor deposition. The deposition of the second bio-compatible layer 358 may result in a conformal coating over the assembled components. Moreover, in an example, 35 grams of a polymeric material may be used to form the second bio-compatible layer 358.

The second bio-compatible layer 358 may be deposited to create a continuous layer that spans the entirety of the assembled components. The second bio-compatible layer 358 can span a region that extends beyond a footprint of the assembled components. As a result, the assembled components can be surrounded by portions of the second bio-compatible layer 358 that rest directly on the first bio-compatible layer 310.

Additionally or alternatively, after the second bio-compatible layer 358 is formed over first bio-compatible layer 310, the electronic component 350, the antenna 322, the electrical interconnects 338, the protective layer 348, the electrical contacts 324, and the electrical interconnects 326, the first bio-compatible layer 310 and the second bio-compatible layer 358 may be annealed and/or sintered. With this arrangement, the second bio-compatible layer 358 may bond to the first bio-compatible layer 310.

Moreover, the partially-fabricated device 300*m* may be cleaned before forming the second bio-compatible layer 358 over the first bio-compatible layer 310, the electronic component 350, the antenna 322, the electrical interconnects 338, the protective layer 348, the electrical contacts 324, and the electrical interconnects 326. The partially-fabricated device 300*m* may be cleaned in a variety of ways. For example, the partially-fabricated device 300*m* may be cleaned by rinsing in a fluid, drying with a gas, and baking at a temperature for a time period. In some embodiments, the fluid may include DI water. Moreover, in some embodiments, the gas may include nitrogen. Further, in some embodiments, the temperature may be 90° C. Further still, in some embodiments, the time period may be 60 minutes.

Further, the partially-fabricated device 300*m* may be plasma cleaned before forming the second bio-compatible layer 358 over the first bio-compatible layer 310, the electronic component 350, the antenna 322, the electrical interconnects 338, the protective layer 348, the electrical contacts 324, and the electrical interconnects 326. The partially-fabricated device 300*m* may be plasma cleaned in a variety of ways. For example, the partially-fabricated device 300*m* may be plasma cleaned at a power for a time period. In some embodiments, the power may be high. Moreover, in some embodiments, the time period may be 5 minutes.

Next, an etch mask 362 is formed over a portion 363 of the second bio-compatible layer 358 to provide a partially-fabricated device 300*o*, as shown in FIG. 3*o*. The etch mask 362 may include a variety of materials. For example, the etch mask 362 may include one or more photoresist layers, such as one photoresist layer comprising cyclopentanone. In such an example, the etch mask 362 may be KMPR® sold by Micro Chem. However, in other examples, the etch mask 362 may include one or more metal layers and/or one or more nitride layers.

Moreover, the etch mask 362 may have a variety of thicknesses. For example, the etch mask 362 may have a thickness between 100 to 150 micrometers, such as 120, 130, or 150 micrometers. Other thicknesses of the etch mask 362 are possible as well.

In an example, the etch mask 362 may be formed by spin coating and patterning. However, in other examples, the etch mask 362 may be formed by microfabrication processes such as evaporation and/or sputtering.

The etch mask 362 may be spin coated in a variety of ways. For example, the etch mask 362 may be spin coated in steps. In such an example, a first step may involve placing a first material on the partially-fabricated device 300*n*, applying a spread cycle, applying a spin cycle, and applying a deceleration cycle.

In some embodiments, placing the first material on the partially-fabricated device 300*n* may include pouring (or pipetting) the first material onto the partially-fabricated device 300*n*.

Moreover, in some embodiments, applying the spread cycle may include rotating the partially-fabricated device 300*n* at a first rate for a first time period. And in such embodiments, the first rate may be 500 rpm. And in such embodiments, the first time period may be 5 seconds. With this arrangement, the first material may be spread over the partially-fabricated device 300*n*. The spread cycle may further include accelerating the partially-fabricated device 300*n* at a second rate for a second time period before rotating the partially-fabricated device 300*n* at the first rate for the first time period. In some embodiments, the second rate may be 100 rpm per second. Moreover, in some embodiments, the second time period may be 5 seconds.

Further, in some embodiments, applying the spin cycle may include rotating the partially-fabricated device 300n at a first rate for a first time period. And in such embodiments, the first rate may be 1000 rpm. And in such embodiments, the first time period may be 38 to 118 seconds. With this arrangement, a first portion of the thickness of the etch mask 362 may be formed. The spin cycle may further include accelerating the partially-fabricated device 300n at a second rate for a second time period before rotating the partially-fabricated device 300n at the first rate for the first time period. In some embodiments, the second rate may be 500 rpm per second. Moreover, in some embodiments, the second time period may be 2 seconds.

Further still, in some embodiments, applying the deceleration cycle comprises decelerating the partially-fabricated device 300n at a rate for a time period. And in such embodiments, the rate may be 500 rpm per second. And in such embodiments, the time period may be 2 seconds.

Moreover, in some embodiments, the partially-fabricated device 300n may be placed in a vacuum chuck before placing the first material on the partially-fabricated device 300m.

The first step may further involve baking the first material at a temperature for a time period. In some embodiments, the temperature is 90° C. Moreover, in some embodiments, the time period may be 5 minutes.

In such an example, a second step may involve placing a second material on the first material, applying a spread cycle, applying a spin cycle, and applying a deceleration cycle.

In some embodiments, placing the second material on the first material may include pouring (or pipetting) the second material onto the first material.

Moreover, in some embodiments, applying the spread cycle may include rotating the partially-fabricated device 300n at a first rate for a first time period. And in such embodiments, the first rate may be 500 rpm. And in such embodiments, the first time period may be 5 seconds. With this arrangement, the second material may be spread over the first material. The spread cycle may further include accelerating the partially-fabricated device 300n at a second rate for a second time period before rotating the partially-fabricated device 300n at the first rate for the first time period. In some embodiments, the second rate may be 100 rpm per second. Moreover, in some embodiments, the second time period may be 5 seconds.

Further, in some embodiments, applying the spin cycle may include rotating the partially-fabricated device 300n at a first rate for a first time period. And in such embodiments, the first rate may be 1000 rpm. And in such embodiments, the first time period may be 38 to 118 seconds. With this arrangement, a second portion of the thickness of the etch mask 362 may be formed. The spin cycle may further include accelerating the partially-fabricated device 300n at a second rate for a second time period before rotating the partially-fabricated device 300n at the first rate for the first time period. In some embodiments, the second rate may be 500 rpm per second. Moreover, in some embodiments, the second time period may be 2 seconds.

Further still, in some embodiments, applying deceleration cycle comprises decelerating the partially-fabricated device 300n at a rate for a time period. And in such embodiments, the rate may be 500 rpm per second. And in such embodiments, the time period may be 2 seconds.

And in some embodiments, the partially-fabricated device 300n may be removed from the vacuum chuck after applying the deceleration cycle.

After the first and second material is spin coated, the first and second material may be baked at a first temperature to a second temperature at a rate for a time period. In some embodiments, the first temperature is 65° C. Moreover, in some embodiments, the second temperature is 90° to 95° C. Further, in some embodiments, the rate is 120° C. per hour. Further still, in some embodiments, the time period may be 1 hour. In another example, the first and second material may be baked at 90° C. for 1 hour.

After the first and second material is baked, the first and second material may be cooled to room temperature at a rate. In some embodiments, the rate is 450° C. per hour or 120° C. per hour.

The etch mask may 362 be patterned in a variety of ways. For example, the first and second material may be patterned by exposing and developing. And, in such an example, the first and second material may be exposed and developed in steps.

In such an example, a first step may involve exposing the first and second material to light at an intensity for a first time period. In some embodiments, the light may be ultra violet light (UV light) that may be generated by a mercury lamp. Moreover, in some embodiments, the intensity may be the intensity may be 16 to 19 mW/cm$^2$. Further, in some embodiments, the first time period may be 30 seconds. Moreover, in such an example, a second step may involve repeating the first step. In another example, the first time period may include one or more cycles (e.g., 3 cycles) where each of the one or more cycles includes an exposure time period (e.g., 20 seconds) and a waiting time period (e.g., 30 seconds to 2 minutes)

Further, in such an example, a third step may involve baking the first and second material at a temperature for a second time period. In some embodiments, the temperature may be 90° C. Moreover, in some embodiments, the second time period may be 2 minutes. Further still, in such an example, a fourth step may involve developing the first and second material using a fluid comprising 1-methoxy-2-propyl acetate. In such an example, the fluid may be SU-8 Developer® sold by Micro Chem. In some embodiments, the time period may be 15 or 10 minutes.

Moreover, the partially-fabricated device 300o may be further processed after formation of the etch mask 362 over the portion 363 of the second bio-compatible layer 358. The partially-fabricated device 300o may be further processed in a variety of ways. For example, the partially-fabricated device 300o may be further processed by rinsing in a fluid, blow drying with a gas, and baking at a temperature for a time period. In some embodiments, the fluid may include IPA. Moreover, in some embodiments, the gas may include nitrogen. Further, in some embodiments, the temperature may be 90° C. Further still, in some embodiments, the time period may be 60 minutes.

Moreover, the partially-fabricated device 300n may be cleaned before forming the etch mask 362 over the portion 363 of the second bio-compatible layer 358. The partially-fabricated device 300n may be cleaned in a variety of ways. For example, the partially-fabricated device 300n may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further, the partially-fabricated device 300n may be baked before forming the etch mask 362 over the portion 363 of the second bio-compatible layer 358. The partially-fabricated device 300n may be baked in a variety of ways. For example, the partially-fabricated device 300m may be baked at a temperature for a time period. In some embodiments, the temperature may be 90° C. Moreover, in some embodiments, the time period may be 5 minutes. Further, in some embodiments, the partially-fabricated device 300n may be baked on a hot plate. After the partially-fabricated device 300n is baked, the partially-fabricated device 300b may be cooled to room temperature.

As shown in FIG. 3p, exposed portions 364 of the second bio-compatible layer 358 (i.e., the portions that are not covered by the etch mask 362) are removed to provide a partially-fabricated device 300p. In an example, the exposed portions 364 of the second bio-compatible layer 358 are removed by etching using an inductively coupled plasma at a power for a time period. In some embodiments, the inductively coupled plasma may include an oxygen plasma. Moreover, in some embodiments, the power may be 400 W at a 300 W bias. Further, in some embodiments, the time period may be 33 minutes. And, in such an example, the etching may comprise one or more cycles that comprises an etch period followed by a rest period, such that the partially-fabricated device 300o may cool down. In some embodiments, the etch period may be 3 minutes. Moreover, in some embodiments, the rest period may be 2 minutes. Further, in some embodiments, the one or more cycles may be 11 cycles. And, in some embodiments, the one or more cycles may be applied in sequence. Other plasmas and/or types of plasmas may be used as well, such as a plasma asher, a reactive ion etcher, etc.

In such an example, a first portion 364A of the exposed portions 364 of the second bio-compatible layer 358 that is located above the protective layer 348 is etched to thereby form an opening 370 in the second bio-compatible layer 358. In some embodiments, the opening 370 may have a dimension of between 500 to 700 micrometers. The opening 370 may have a variety of shapes, such as a square shape with rounded corners, a rectangular shape, a circular shape, etc.

Moreover, in such an example, a second portion 364B of the exposed portions 364 of the second bio-compatible layer 358 (and corresponding portions of the first-bio-compatible layer 310) is etched, such that a portion 374 of the sacrificial layer 304 is exposed. The portion 374 of the sacrificial layer 304 that is exposed may be referred to as a release region.

In other examples (not shown), when the second portion 364B of the exposed portions 364 of the second bio-compatible layer 358 (and corresponding portions of the first-bio-compatible layer 310) is etched, the portion 374 of the sacrificial layer 304 may be etched.

Additionally, the etching of the second portion 364B of the exposed portions 364 of the second bio-compatible layer 358 (and corresponding portions of the first bio-compatible layer 310) leaves excess material 372. With this approach, the etch mask 362 may define a shape 366 of the bio-compatible device and/or a shape 368 of the antenna 322.

Further, as illustrated in FIG. 3p, at least a portion of the protective layer 348 is removed thereby leaving a portion 348B of the protective layer 348. In an example, the portion 348B of the protective layer 348 is removed by the inductively coupled plasma that etches the exposed portions 364 of the second bio-compatible layer 358. In some embodiments, the portion 348B of the protective layer 348 that is etched may have a thickness between 20 and 30 micrometers. And, as illustrated in FIG. 3p, at least a portion of the etch mask 362 is removed thereby leaving a portion 362B of the etch mask 362. In an example, the portion 362B of the etch mask 362 is removed by the inductively coupled plasma that etches the exposed portions 364 of the second bio-compatible layer 358.

Next, the portion 348B of the protective layer 348 is removed to thereby expose the sensor electrodes 340 to provide a partially-fabricated device 300q, as shown in FIG. 3q. The portion 348B of the protective layer 348 may be removed in a variety of ways. For example, the portion 348B of the protective layer 348 may be removed by dissolving the portion 348B of the protective layer 348 in a fluid at temperature for a time period. In some embodiments, the fluid may comprise n-methyl pyrrolidinone. And in such embodiments, the fluid may be Remover PG® sold by Micro Chem. Moreover, in some embodiments, the temperature may be 90° C. Further, in some embodiments, the time period may be 5 minutes.

Moreover, in an example, removal may further involve rinsing in a fluid and drying with a gas. In some embodiments, the fluid may include IPA. Moreover, in some embodiments, the gas may include nitrogen.

As shown in FIG. 3r, the sacrificial layer 304 is removed to release the bio-compatible device 300r from the working substrate 302. The sacrificial layer 304 may be removed in a variety of ways. For example, the sacrificial layer 304 may be removed by dissolving the sacrificial layer 304 in a fluid at a temperature for a time period. In some embodiments, the sacrificial layer 304 may be dissolved in the fluid through the portion 374 of the sacrificial layer 304 that is exposed (or that was etched when the second portion 364B of the exposed portions 364 of the second bio-compatible layer 358 (and the corresponding portions of the first bio-compatible layer 310) is etched using the inductively coupled plasma). As another example, the sacrificial layer 304 may be removed by etching (e.g., wet etching) using an etchant that might not etch the second bio-compatible layer 358, the first bio-compatible layer 310, and/or the conductive pattern 342.

Moreover, in an example, removal may further involve soaking in a fluid, rinsing with the fluid, and drying. In some embodiments, the fluid may include DI water. Moreover, in some embodiments, drying may involve hand drying on a towel.

As illustrated in FIG. 3r, the bio-compatible device 300r includes the first bio-compatible layer 310, the antenna 322, the electrical contacts 324, the electrical interconnects 326, the electrical interconnects 338, the sensor electrodes 340, the second bio-compatible layer 358, the opening 370, the first side 312 of the bio-compatible device, and the second side 360 of the bio-compatible device. The first bio-compatible layer 310 and the second bio-compatible layer 358 encapsulates the assembled components, except the sensor electrodes 340 are exposed by the opening 370.

The bio-compatible device 300r is suitable for incorporation into a biological environment, such as within a body-mountable device or an implantable medical device, for example. Due to the encapsulating bio-compatible material, the surrounding environment is sealed from the embedded components. For example, if the bio-compatible device 300r is implanted in a biological host, or placed in an eye-mountable device to be exposed to tear fluid, the bio-compatible device 300r is able to be exposed to fluids of the biological host (e.g., tear fluid, blood, etc.), because the entire exterior surface is coated with bio-compatible material, except that the sensor electrodes 340 are exposed to allow detection of one or more analytes in the fluid.

The description in FIGS. 3a-r describes one example of a process for fabricating a bio-compatible device that can be embedded in an eye-mountable device. However, the process described with reference to FIGS. 3a-r may be employed to create bio-compatible devices for other applications, such as other mountable devices or implantable electronic medical device applications. Such implantable electronic medical devices may include an antenna for communicating information (e.g., sensor results) and/or inductively harvesting energy (e.g., radio frequency radiation). Implantable electronic medical devices may also include electrochemical sensors or they may include other electronic devices. The process described with reference to FIGS. 3a-r may be used to create bio-compatible devices suitable to be mounted on or in another part of the body, such as the skin, a tooth, or on a tissue in the mouth, for example.

FIGS. 4a-d illustrate example sensor electrodes that may be formed when forming the sensor electrodes 340 on the second metal layer 436. Each of the example sensor electrodes described herein may be formed in the process described with reference to FIG. 3i. The illustrations shown in FIGS. 4a-d are generally shown in cross-section view to illustrate formed layers developed to create a sensor electrode. The dimensions, including relative thicknesses and widths, of the various layers illustrated and described in connection with FIGS. 4a-d are not illustrated to scale. Instead, the drawings in FIGS. 4a-d illustrate the various layers for purposes of explanation only.

Figure 4A:
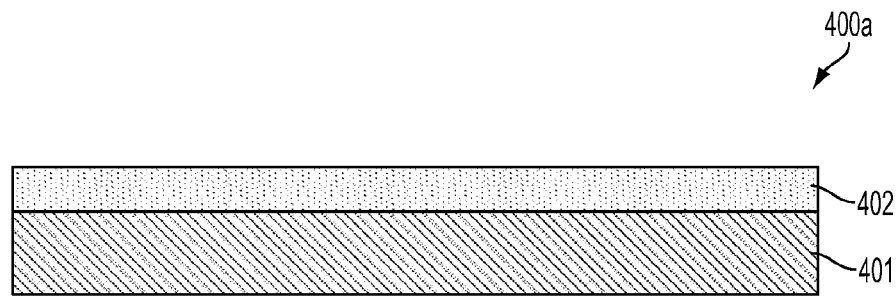
FIGS. 4a-d shows example cross-sections of a sensor electrode, according to an example embodiment.

FIG. 4a illustrates a sensor electrode 400a with a first conductive layer 401 of a first metal and a second conductive layer 402 of a second metal over first conductive layer 401. In FIG. 4a, the second conductive layer 402 is a continuous layer. In an example, the first metal is gold, and the second metal is platinum. Other metals could be used. In general, however, the first metal is more malleable and less prone to cracking than the second metal.

Figure 4B:
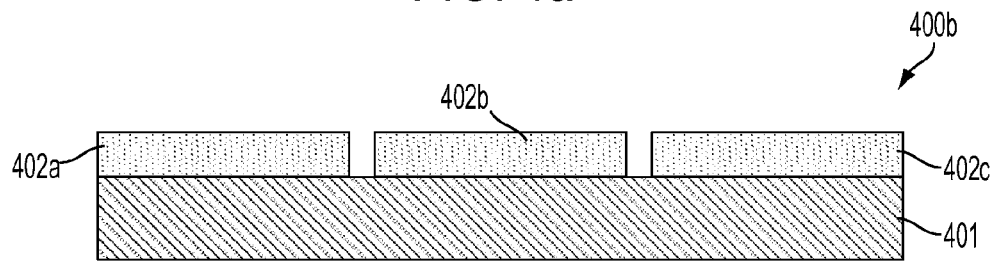

In some embodiments, the second conductive layer 402 may not need to be continuous. The second conductive layer 402 may be segmented to minimize the amount of the second metal used to form the sensor electrodes 340. FIG. 4b illustrates a sensor electrode 400b in which the second conductive layer 402 of the electrode 400a is formed as second conductive layer segment 402a-c. The second conductive layer segments 402a-c may provide sufficient surface area for oxidation reactions or reduction reactions at the sensor electrodes 340 while using less of the second metal than is used in the second conductive layer 402. Further, with gaps 404a-b between the second conductive layer segments 402a-c, the second conductive layer segments 402a-c may be less prone to cracking than the second conductive layer 402.

Figure 4C:
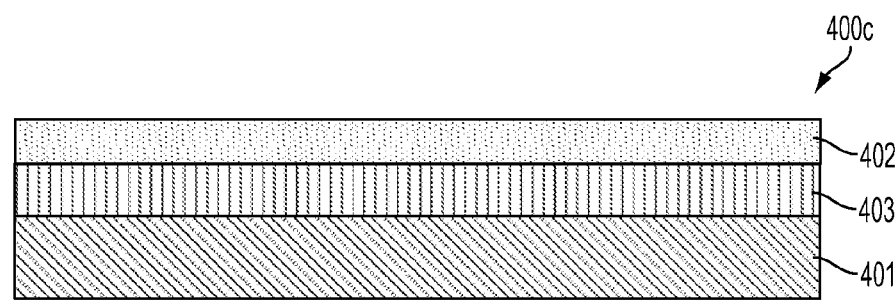
Figure 4D:
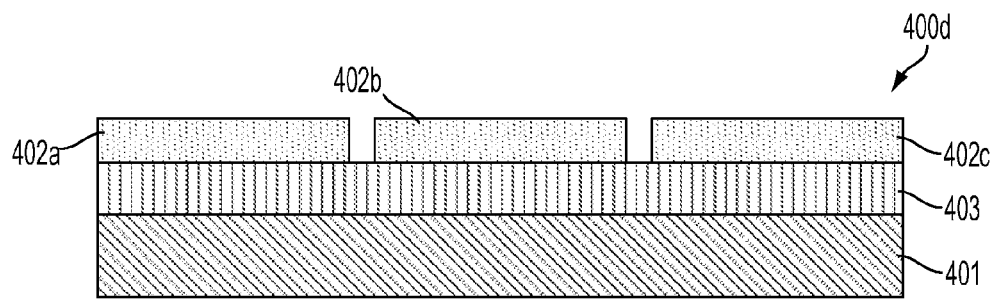

Moreover, the sensor electrodes 340 may include more than two layers. FIG. 4c illustrates a sensor electrode 400c in which a third conductive layer 403 of a third metal is between first conductive layer 401 and second conductive layer 402. FIG. 4d illustrates a sensor electrode 400d in which a third conductive layer 403 of a third metal is between first conductive layer 401 and second conductive layer segments 402a-c. The third conductive layer 403 may provide additional structure for the sensor electrodes. For example, the third metal may be selected to provide a strong bond between the first and second metals; thus, if the first metal is gold and the second metal is platinum, the third metal could be palladium. In yet other examples, the sensor electrodes may include more than three layers.

Figure 5:
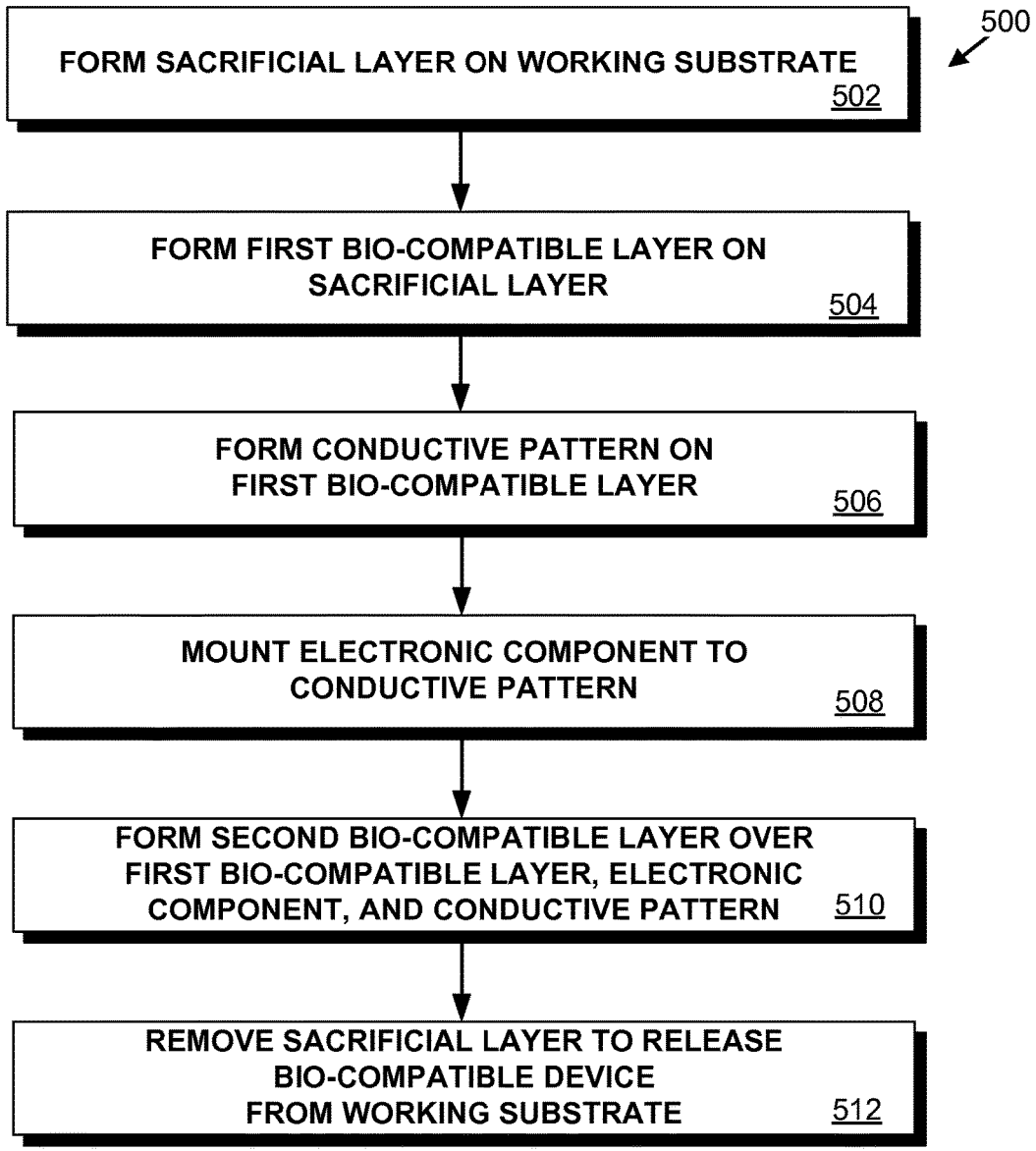
FIG. 5 is a flow chart illustrating a method for fabricating a bio-compatible device, according to an example embodiment.

FIG. 5 is a flowchart of a method 500 for fabricating a bio-compatible device, according to an example embodiment. The method 500 may involve forming a sacrificial layer on a working substrate (block 502). The sacrificial layer may be the same as or similar to the sacrificial layer 304. Moreover, the sacrificial layer may be formed the same or similar way as the sacrificial layer may be formed as described with reference to FIG. 3a. The working substrate may be the same as or similar to the working substrate 302.

For instance, in some embodiments, the sacrificial layer may comprise one or more metal layers. Moreover, in some embodiments, the sacrificial layer may comprise one or more photoresist layers. Further, in some embodiments, the sacrificial layer may comprise at least one photoresist layer that is patterned negatively. Further still, in some embodiments, the sacrificial layer may comprise at least one photoresist layer that is patterned positively. Moreover, in some embodiments, the sacrificial layer may comprise one or more metal layers formed over one or more photoresist layers. Further, in some embodiments, the sacrificial layer may comprise one or more photoresist layers formed over one or more metal layers. Further still, in some embodiments, the sacrificial layer may comprise one or more materials selected from the group consisting of aluminum, titanium, chromium, 1-methoxy-2-propanol acetate, 2-ethoxyethyl acetate, and cyclohexanone. And, in some embodiments, when the sacrificial layer comprises one or more photoresist layers and one or more metal layers, at least one photoresist layer of the one or more photoresists layers may be thicker than at least one metal layer of the one or more metal layers.

The method 500 may involve forming a first bio-compatible layer on the sacrificial layer such that the first bio-compatible layer adheres to the sacrificial layer (block 504). The first bio-compatible layer defines a first side of a bio-compatible device. The first bio-compatible layer may be the same as or similar to the first bio-compatible layer 310. Moreover, the first bio-compatible layer may be formed the same or similar way as the first bio-compatible layer 310 may be formed as described with reference to FIG. 3b. For instance, in some embodiments, when the sacrificial layer comprises one or more metal layers, the first bio-compatible layer may adhere to at least one metal layer of the one or more metal layers via hydrogen bonds.

The method 500 may involve forming a conductive pattern on the first bio-compatible layer (block 506). The conductive pattern defines an antenna, sensor electrodes, electrical contacts, and one or more electrical interconnects. The conductive pattern may be the same as or similar to the conductive pattern 342, the antenna may be the same as or similar to the antenna 322, the electrical contacts may be the same as or similar to the electrical contacts 324, and the one or more electrical interconnects may be the same as or similar to the electrical interconnects 326 and/or the electrical interconnects 338. Further, the sensor electrodes may include at least one of the sensor electrodes 340 and/or any of the sensor electrodes 400a-d.

The method 500 may involve mounting an electronic component to the conductive pattern (block 508). The electronic component may be the same as or similar to the electronic component 350. In some embodiments, mounting the electronic component to the conductive pattern may involve mounting the electronic component to the electrical contacts. Moreover, in at least one such embodiment, the electronic component may be mounted to the electrical contacts the same or similar way as the electronic component 350 may be mounted to the electrical contacts 324 as described with reference to FIG. 3l.

For instance, in some embodiments, when the sacrificial layer comprises one or more photoresist layers, at least one photoresist layer of the one or more photoresist layers may be aligned with a location of the first bio-compatible layer where the electronic component is mounted to the conductive pattern. Moreover, in at least one such embodiment, the at least one photoresist layer may have at least one dimension that is greater than a corresponding dimension of the electronic component. Further, in at least one such embodiment, when the sacrificial layer further comprises one or more metal layers, the at least one photoresist layer may be formed over at least one metal layer of the one or more metal layers. Further still, in at least one such embodiment, when the sacrificial layer further comprises one or more metal layers, at least one metal layer of the one or more metal layers may be formed over the at least one photoresist layer.

The method 500 may involve forming a second bio-compatible layer over the first bio-compatible layer, the electronic component, and the conductive pattern (block 510). The second bio-compatible layer defines a second side of the bio-compatible device. The second bio-compatible layer may be the same as or similar to the second bio-compatible layer 358. Moreover, the second bio-compatible layer may be formed the same or similar way to as the second bio-compatible layer 358 may be formed as described with reference to FIG. 3n.

The method 500 may involve removing the sacrificial layer to release the bio-compatible device from the working substrate (block 512). The sacrificial layer may be removed to release the bio-compatible device from the working substrate the same or similar way as the sacrificial layer 304 may be removed to release the bio-compatible device 300r from the working substrate 302 as described with reference to FIG. 3r.

For instance, in some embodiments, removing the sacrificial layer to release the bio-compatible device from the working substrate may involve etching a portion of the second and first bio-compatible layers using an inductively coupled plasma, such that a portion of the sacrificial layer is exposed, and dissolving the sacrificial layer in a fluid. Moreover, in at least one such embodiment, the portion of the sacrificial layer that is exposed may be the same as or similar to the portion 374 of the sacrificial layer 304 that is exposed. And, the portion of the second and first bio-compatible layers may be etched using an inductively coupled plasma, such that the portion of the sacrificial layer is exposed, the same or similar way as the portion the portion 364B of the exposed portions 364 of the second bio-compatible layer 358 (and corresponding portions of the first bio-compatible layer 310) may be etched, such that the portion 374 of the sacrificial layer 304 is exposed, as described with reference to FIG. 3p. Further, in at least one such embodiment, the fluid may comprise potassium borates and/or 1-methyl-2-pyrrolidone.

Moreover, in some embodiments, removing the sacrificial layer to release the bio-compatible device from the working substrate may comprise etching the sacrificial layer.

Further, in some embodiments, removing the sacrificial layer to release the bio-compatible device from the working substrate may involve etching a portion of the second and first bio-compatible layers and a first portion of the sacrificial layer using an inductively coupled plasma, and dissolving a second portion of the sacrificial layer in a fluid. Moreover, in at least one such embodiment, the first portion of the sacrificial layer that is etched may be the same as or similar to the portion 374 of the sacrificial layer 304 that is etched. And, the portion of the second and first bio-compatible layers and the first portion of the sacrificial layer may be etched using an inductively coupled plasma, the same or similar way as the portion the portion 364B of the exposed portions 364 of the second bio-compatible layer 358 (and corresponding portions of the first bio-compatible layer 310) and the portion 374 of the sacrificial layer may be etched, as described with reference to FIG. 3p. Further, in at least one such embodiment, the fluid may comprise potassium borates and/or 1-methyl-2-pyrrolidone.

Further still, in some embodiments, when the sacrificial layer comprises one or more photoresist layers, removing the sacrificial layer to release the bio-compatible device from the working substrate may comprise etching under at least one photoresist layer of the one or more photoresist layers.

Further, the method 500 may further involve forming a protective layer over the sensor electrodes, such that the sensor electrodes are covered by the protective layer. The protective layer may be the same as or similar to the protective layer 348. Moreover, the protective layer may be formed the same or similar way as the protective layer 348 may be formed as described with reference to FIG. 3k.

Further still, the method 500 may further involve removing a portion of the second bio-compatible layer to form an opening in the second bio-compatible layer. The opening may be the same as or similar to the opening 370. The portion of the second bio-compatible layer may be removed to form an opening in the second bio-compatible layer the same or similar way as a portion of the second bio-compatible layer 358 may be removed to form the opening 370 in the second bio-compatible layer 358 as described with reference to FIGS. 3o-p.

Moreover, in some embodiments, removing a portion of the second bio-compatible layer to form an opening in the second bio-compatible layer may comprise forming an etch mask over the second bio-compatible layer, wherein the etch mask exposes the portion of the second bio-compatible layer; and etching, using an inductively coupled plasma, the portion of the second bio-compatible layer exposed by the etch mask to thereby form the opening. Further, in some embodiments, the etch mask may define a shape of the bio-compatible device. Further still, in some embodiments, the etch mask may define a shape of the antenna. The etch mask may be same as or similar to the etch mask 362, the shape of the bio-compatible device may be the same as or similar to the shape 366 of the bio-compatible device, the shape of the antenna may be the same as or similar to the shape 368 of the antenna 322, and the inductively coupled plasma may be the same as or similar to the inductively coupled plasma described with reference to FIG. 3o.

Moreover, the method 500 may further involve removing the protective layer through the opening in the second bio-compatible layer to thereby expose the sensor electrodes. The protective layer may be removed through the opening in the second bio-compatible layer to thereby expose the sensor electrodes in the same or similar way as the protective layer 348 may be removed through the opening 370 in the second bio-compatible layer 358 to thereby expose the sensor electrodes 348 as described with reference to FIGS. 3p-q.

For instance, in some embodiments, removing the protective layer through the opening in the second bio-compatible layer to thereby expose the sensor electrodes may comprise etching, using the inductively coupled plasma, at least a portion of the protective layer through the opening in the second bio-compatible layer. Moreover, in some embodiments, removing the protective layer through the opening in the second bio-compatible layer to thereby expose the sensor electrodes may comprise dissolving at least a portion of the protective layer in a fluid. The fluid may be the same as or similar to the fluid used to dissolve the portion 348B of the protective layer 348 described with reference to FIG. 3q.

Figure 6:
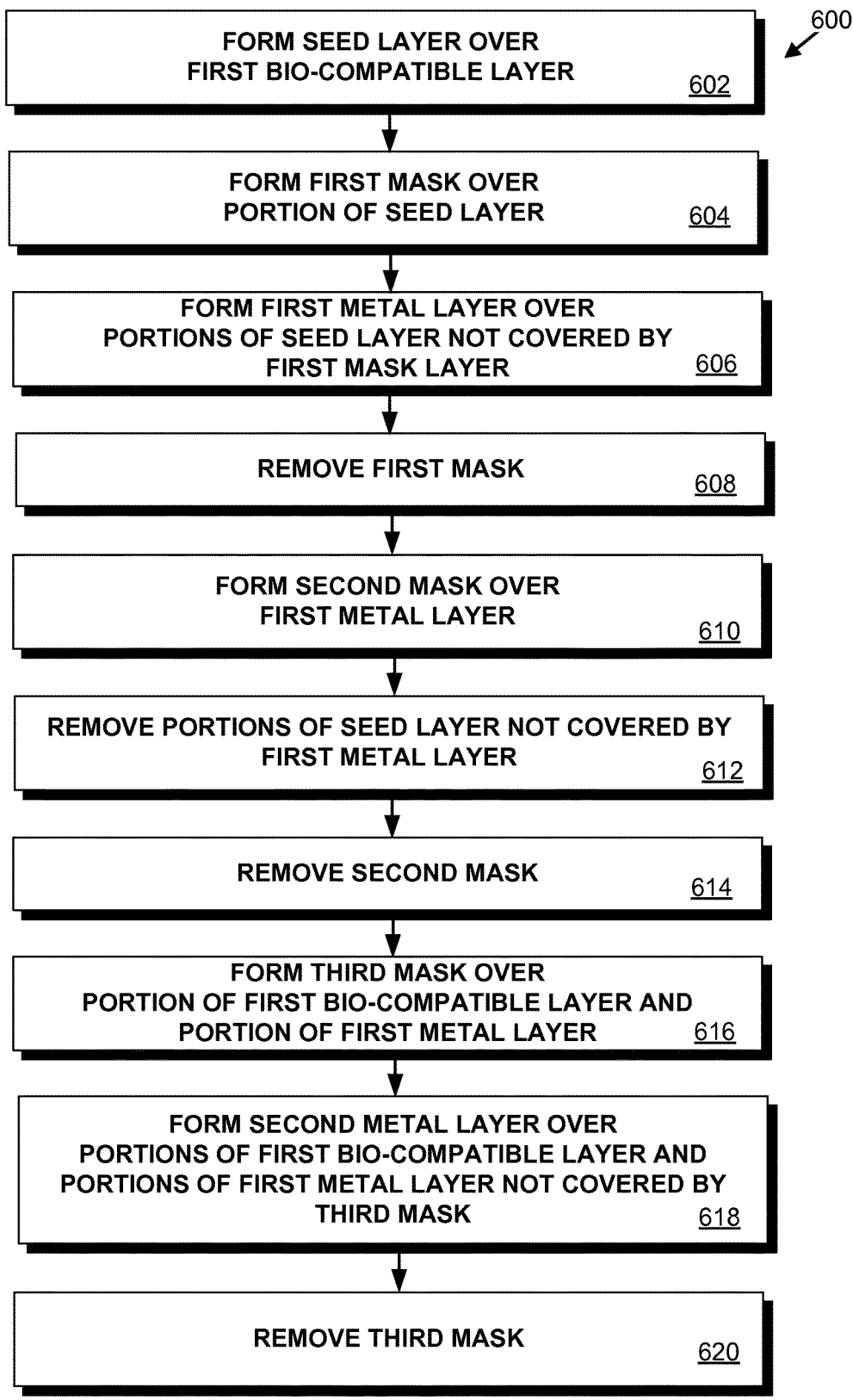
FIG. 6 is a flow chart illustrating a method for forming a conductive pattern, according to an example embodiment.

FIG. 6 is a flow chart illustrating a method 600 for forming a conductive pattern, according to an example embodiment. The method 600 may be performed in connection with block 506 of method 500. The method 600 may involve forming a seed layer over the first bio-compatible layer (block 602). The seed layer may be the same as or similar to the seed layer 314. The seed layer may be formed the same or similar way as the seed layer 314 may be formed as described with reference to FIG. 3c.

The method 600 may involve forming a first mask over a portion of the seed layer (block 1204). The first mask may be the same as or similar to the first mask 316. The first mask may be formed the same or similar way as the first mask 316 may be formed as described with reference to FIG. 3d.

The method 600 may involve forming a first metal layer over portions of the seed layer not covered by the first sacrificial layer (block 606). The first metal layer defines the antenna, the electrical contacts, and at least one electrical interconnects of the one or more electrical interconnects. The first metal layer may be the same as or similar to the first metal layer 320. The first metal layer may be formed the same or similar way as the first metal layer 320 may be formed as described with reference to FIG. 3e.

The method 600 may involve removing the first mask (block 608). The first mask may be removed in the same or similar way as the first mask 316 may be removed as described with reference to FIG. 3f.

The method 600 may involve forming a second mask over the first metal layer (block 610). The second mask may be the same as or similar to the second mask 329. The second mask may be formed the same or similar way as the second mask 329 may be formed as described with reference to FIG. 3f.

The method 600 may involve removing portions of the seed layer not covered by the first metal layer (block 612). The portions of the seed layer not covered by the first metal layer may be removed the same or similar way as the portion 318 of the seed layer 314 may be removed as described with reference to FIG. 3g.

The method 600 may involve removing the second mask (block 614). The second mask may be removed the same or similar way as the second mask 329 may be removed as described with reference to FIG. 3g.

The method 600 may involve forming a third mask over a portion of the first bio-compatible layer and a portion of the first metal layer (block 616). The third mask may be the same as or similar to the third mask 330. The third mask may be formed the same or similar way as the third mask 330 may be formed as described with reference to FIG. 3h.

The method 600 may involve forming a second metal layer over portions of the first bio-compatible layer and portions of the first metal layer not covered by the third mask (block 618). The second metal layer defines the sensor electrodes and at least one electrical interconnects of the one or more electrical interconnects. The second metal layer may be the same as or similar to the second metal layer 336. The second metal layer may be formed the same or similar way as the second metal layer 336 may be formed as described with reference to FIG. 3i.

The method 600 may involve removing the third mask (block 620). The third mask may be removed the same or similar way as the third mask 330 may be removed as described with reference to FIG. 3j.

Figure 7:
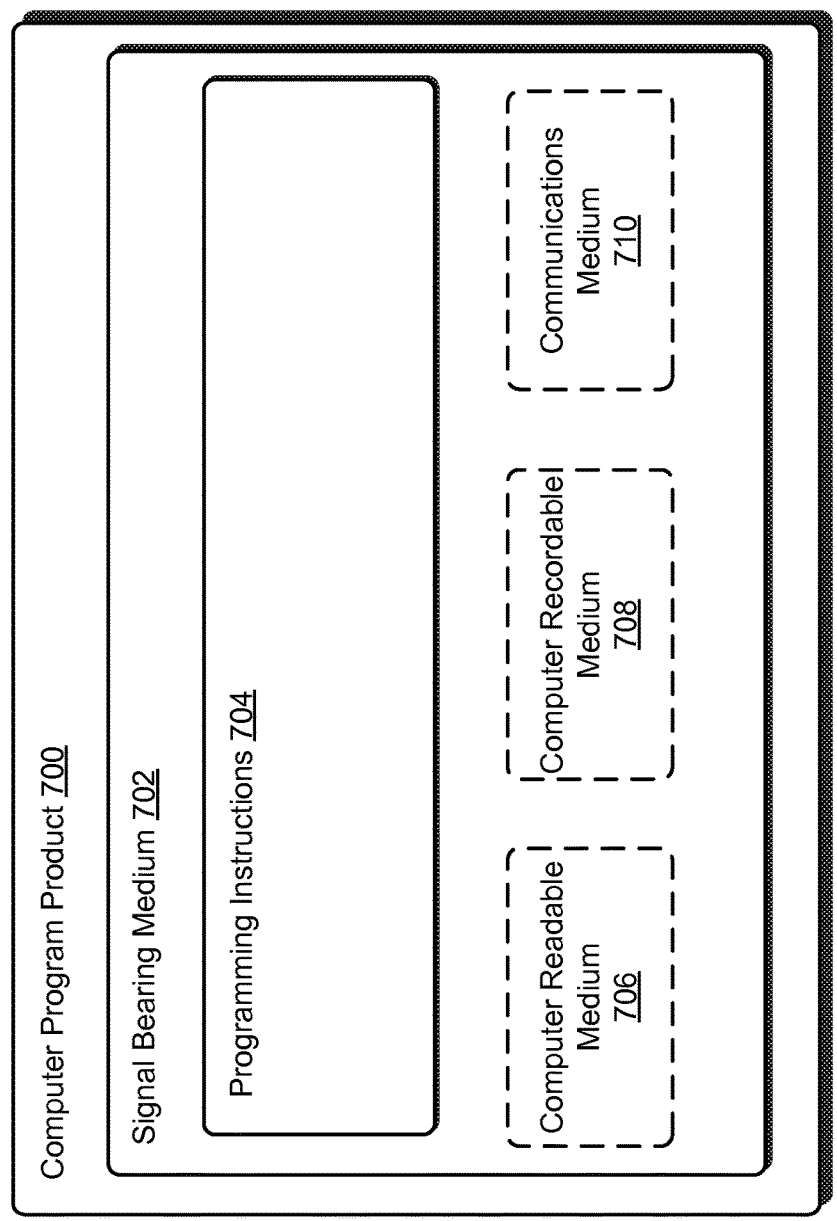
FIG. 7 depicts a computer-readable medium configured according to an example embodiment.

FIG. 7 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause a system to carry out the various functions, tasks, capabilities, etc., described above.

In some embodiments, the disclosed techniques can be implemented by computer program instructions encoded on a non-transitory computer-readable storage media in a machine-readable format, or on other non-transitory media or articles of manufacture. FIG. 7 is a schematic illustrating a conceptual partial view of a computer program product 700 that includes a computer program for executing a computer process on a computing device, to perform any of the methods described herein.

In one embodiment, the computer program product 700 is provided using a signal bearing medium 702. The signal bearing medium 702 may include one or more programming instructions 704 that, when executed by one or more processors may provide functionality or portions of the functionality described above with respect to FIGS. 1-12. In some examples, the signal bearing medium 1302 can include a non-transitory computer-readable medium 706, such as, but not limited to, a hard disk drive, a Compact Disc (CD), a Digital Video Disk (DVD), a digital tape, memory, etc. In some implementations, the signal bearing medium 702 can be a computer recordable medium 708, such as, but not limited to, memory, read/write (R/W) CDs, R/W DVDs, etc. In some implementations, the signal bearing medium 702 can be a communications medium 710, such as, but not limited to, a digital and/or an analog communication medium (e.g., a fiber optic cable, a waveguide, a wired communications link, a wireless communication link, etc.). Thus, for example, the signal bearing medium 702 can be conveyed by a wireless form of the communications medium 710.

The one or more programming instructions 704 can be, for example, computer executable and/or logic implemented instructions. In some examples, a computing device is configured to provide various operations, functions, or actions in response to the programming instructions 704 conveyed to the computing device by one or more of the computer readable medium 706, the computer recordable medium 708, and/or the communications medium 710.

The non-transitory computer readable medium 706 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

We claim:

1. A method comprising:
    forming a conductive pattern on a bio-compatible layer to provide at least one sensor electrode, wherein forming the conductive pattern comprises: (i) forming a first conductive layer by forming a continuous layer of a first metal on a portion of the bio-compatible layer and (ii) forming a second conductive layer by forming a plurality of segments of a second metal over the first conductive layer, such that the first conductive layer is not covered by the second metal between the segments, and wherein the first metal is more malleable than the second metal; and
    mounting an electronic component to the conductive pattern to provide at least an electrochemical sensor for use in a body-mountable device.

2. The method of claim 1, wherein the first metal is gold.

3. The method of claim 1, wherein the second conductive layer provides a surface on which one of an oxidation reaction or a reduction reaction of reactant occurs, and wherein an identity of the second metal depends on at least the reactant.

4. The method of claim 3, wherein the reactant is hydrogen peroxide, and wherein the second metal is platinum.

5. The method of claim 1, wherein the at least one sensor electrode further comprises a third conductive layer comprising a third metal, wherein the third conductive layer is between the first conductive layer and the second conductive layer.

6. The method of claim 5, wherein the third metal is palladium.

7. The method of claim 5, wherein forming the conductive pattern further comprises:
    forming a continuous layer of the third metal over the first conductive layer to provide the third conductive layer.

8. A sensor comprising:
    a conductive pattern on a bio-compatible surface comprising at least one sensor electrode that includes (i) a first conductive layer comprising a continuous layer of a first metal and (ii) a second conductive layer comprising a plurality of segments of a second metal over the first conductive layer, wherein the first conductive layer is not covered by the second metal between the segments, and wherein the first metal is more malleable than the second metal; and
    an electronic component mounted to the conductive pattern, wherein the sensor is for use as an electrochemical sensor in a body-mountable device.

9. Theسensor of claim 8, wherein the first metal is gold.

10. The sensor of claim 8, wherein the second conductive layer provides a surface on which one of an oxidation reaction or a reduction reaction of reactant occurs, and wherein an identity of the second metal depends on at least the reactant.

11. The sensor of claim 10, wherein the second metal is platinum.

12. The sensor of claim 8, wherein the at least one sensor electrode further comprises a third conductive layer comprising a third metal, wherein the third conductive layer is between the first conductive layer and the second conductive layer.

13. The sensor of claim 12, wherein the third metal is palladium.

14. The sensor of claim 12, wherein the third conductive layer comprises a continuous layer of the third metal.

* * * * *